US011776663B2

(12) United States Patent
Rizk

(10) Patent No.: US 11,776,663 B2
(45) Date of Patent: *Oct. 3, 2023

(54) QUALITY SCORE COMPRESSION

(71) Applicant: Illumina, Inc., San Diego, CA (US)

(72) Inventor: Guillaume Alexandre Pascal Rizk, Rennes (FR)

(73) Assignee: Illumina, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/974,978

(22) Filed: Oct. 27, 2022

(65) Prior Publication Data

US 2023/0040143 A1   Feb. 9, 2023

Related U.S. Application Data

(63) Continuation of application No. 17/520,615, filed on Nov. 5, 2021, now Pat. No. 11,527,307.

(60) Provisional application No. 63/110,308, filed on Nov. 5, 2020.

(51) Int. Cl.
*H03M 7/00* (2006.01)
*G16B 50/50* (2019.01)
*H03M 7/30* (2006.01)

(52) U.S. Cl.
CPC .......... *G16B 50/50* (2019.02); *H03M 7/3071* (2013.01); *H03M 7/6011* (2013.01)

(58) Field of Classification Search
CPC ... G16B 50/50; H03M 7/3071; H03M 7/6011; H03M 7/00; H03M 7/34; H03M 7/38
USPC ..................................................... 341/50, 51
See application file for complete search history.

(56) References Cited

U.S. PATENT DOCUMENTS

| 8,847,799 | B1 | 9/2014 | Kennedy et al. |
| 10,090,857 | B2 | 10/2018 | Bhola et al. |
| 11,527,307 | B2 * | 12/2022 | Rizk .................... H03M 7/6011 |
| 2011/0288785 | A1 | 11/2011 | Tembe |
| 2013/0031092 | A1 | 1/2013 | Bhola et al. |
| 2014/0361911 | A1 | 12/2014 | Kennedy et al. |
| 2015/0149510 | A1 | 5/2015 | Kennedy et al. |
| 2016/0154795 | A1 | 6/2016 | Kennedy et al. |
| 2017/0116216 | A1 | 4/2017 | Kennedy et al. |
| 2017/0124254 | A1 | 5/2017 | Rooyen et al. |
| 2017/0357665 | A1 | 12/2017 | Olivares-Amaya et al. |

(Continued)

OTHER PUBLICATIONS

[No Author] "Chap 5 Dictionary Techniques," Aug. 23, 2016 from URL <http://se.csie.dyu.edu.tw/lairrol/files/DC/chap5 .pdf>, 55 pages.

(Continued)

*Primary Examiner* — Jean B Jeanglaude
(74) *Attorney, Agent, or Firm* — Fish & Richardson P.C.

(57) ABSTRACT

Methods, systems, and computer programs for compressing nucleic acid sequence data. A method can include obtaining nucleic acid sequence data representing: (i) a read sequence, and (ii) a plurality of quality scores, determining whether the read sequence includes at least one "N" base, based on a determination that the read sequence includes at least one "N" base, generating, by one or more computers, a first encoding data set by using a first encoding process to encode each set of four quality scores of the read sequence into a single byte of memory, and using a second encoding process to encode the first encoded data set, thereby compressing the data to be compressed.

20 Claims, 10 Drawing Sheets

(56) References Cited

U.S. PATENT DOCUMENTS

2018/0152535 A1\* 5/2018 Sade ............... G16B 50/50
2022/0139502 A1 5/2022 Rizk et al.

OTHER PUBLICATIONS

[No Author] "Histoiy of Lossless Data Compression Algorithms," Jul. 28, 2014 from URL <http://ieeeghn.org/wiki/index.php?title=Histoiy_of_Lossless_Data_Co+A7mpression_Algorithms&oldid=96464&printable=yes&useskin=vector>, 16 pages.

Benoit et al., "NGS Data Compression.," Algorithms for Next-Generation Sequencing Data, Dec. 2017, 91-115.

Cánovas et al., "Lossy compression of quality scores in genomic data," Biointoimatics, Aug. 1, 2014, 30(15):2130-6.

Hach et al., "SCALCE: boosting sequence compression algorithms using locally consistent encoding," Bioinformatics, Dec. 1, 2012, 28(23):3051-7.

Nalbantoglu et al., "Compression of Next Generation Sequencing Data," DCC, Apr. 7, 2015, 10 pages.

PCT International Search Report and Written Opinion in International Appln. No. PCT/US2021/058364, dated Feb. 23, 2022, 19 pages.

Wan et al., "Transformations for the compression of FASTQ quality scores of next-generation sequencing data," Bioinformatics, Mar. 1, 2012, 28(5):628-35.

wikipedia.org, "Arithmetic coding," Oct. 29, 2020 from URL <https://en.wikipedia.org/w/index.php?title=Arithmetic_coding&oldid=985967562>, 14 pages.

\* cited by examiner

500

```
┌─────────────────────────────────────────────┐
│ OBTAIN A FIRST ENCODING DATA SET GENERATED BY│
│ ENCODING EACH OF A PLURALITY OF QUALITY     │
│ SCORES USING A BASE-X NUMBER, WHERE X IS AN │
│ INTEGER NUMBER REPRESENTING A NUMBER OF     │
│ DIFFERENT QUALITY SCORES USED BY THE GENETIC│
│ SEQUENCING DEVICE                       502 │
└─────────────────────────────────────────────┘
                      ▼
┌─────────────────────────────────────────────┐
│ GENERATE A FIRST DECODED DATA SET USING THE │
│ BASE-X NUMBER                           504 │
└─────────────────────────────────────────────┘
                      ▼
┌─────────────────────────────────────────────┐
│ ORDER THE FIRST DECODED DATA SET WITHIN ONE │
│ OR MORE OTHER DECODED DATA SETS         506 │
└─────────────────────────────────────────────┘
                      ▼
┌─────────────────────────────────────────────┐
│ GENERATE AN AGGREGATE DECODED DATA SET      │
│ BASED ON THE FIRST DECODED DATA SET AND THE │
│ ONE OR MORE OTHER DECODED DATA SETS     508 │
└─────────────────────────────────────────────┘
```

FIG. 5

QUALITY SCORE COMPRESSION

CROSS-REFERENCE TO RELATED APPLICATIONS

This application is a continuation of and claims priority to U.S. application Ser. No. 17/520,615 filed Nov. 5, 2021, which claims the benefit of U.S. Application Ser. No. 63/110,308 filed on Nov. 5, 2020, the entire contents of which are incorporated herein by reference.

BACKGROUND

In some cases, genomic sequencing describes a method of identifying nucleotides or other component parts of genomic data. Computers can be used to analyze one or more sets of the genomic data and correlate a collection of component parts, such as nucleotides, with their respective positions in a given reference genome. In this way, a computer can "map" the collection of molecular markers onto the reference genome.

SUMMARY

In general, the present disclosure relates to methods, systems, and computer programs for the compression of quality scores generated by a sequencing engine based on genomic data. In one implementation, the quality scores generated by the sequencing engine based on genomic data can initially be compressed by grouping one or more quality scores into a single data item within a sequence of data items representing the set of quality scores. The sequence of data items can then be further compressed or encoded into a final compressed form.

According to one innovative aspect of the present disclosure, a method for compressing nucleic acid sequence data is disclosed. In one aspect, the method can include obtaining, by one or more computers, nucleic acid sequence data representing (i) a read sequence comprising data that corresponds to a plurality of base calls generated by a nucleic acid sequencing device, and (ii) a plurality of quality scores, wherein each quality score of the plurality of quality scores indicates a likelihood that a particular base call of the read sequence was correctly generated by a nucleic acid sequencing device, determining, by one or more computers, whether the read sequence includes at least one "N" base, based on a determination that the read sequence does not include at least one "N" base, generating, by one or more computers, a first encoded data set by using a first encoding process to encode each of the quality scores of the read sequence using a base-(x minus 1) number, where x is an integer representing a number of different quality scores used by the nucleic acid sequencing device, and using, by one or more computers, a second encoding process to encode the first encoded data set, thereby compressing the data to be compressed.

Other versions include corresponding systems, apparatus, and computer programs to perform the actions of methods defined by instructions encoded on computer readable storage devices.

These and other versions may optionally include one or more of the following features. For instance, in some implementations, x is equal to 3.

In some implementations, the first encoding process can include encoding, by one or more computers, each set of five quality scores of the plurality of quality scores of the read sequence into a single byte by representing each quality score of the set of five quality scores as a base-3 number.

In some implementations, the method can further include based on a determination that the read sequence includes at least one "N" base, generating, by one or more computers, a second encoding data set by using a third encoding process to encode each set of four quality scores of the read sequence into a single byte of memory, and using, by one or more computers, a fourth encoding process to encode the second encoding data.

In some implementations, the second encoding process and the fourth encoding process are the same.

In some implementations, the obtained data can include a FASTQ file.

In some implementations, the first encoded data set is a compressed version of the plurality of quality scores.

In some implementations, the second encoding process is a compression process.

In some implementations, the compression process comprises a Prediction by Partial Matching (PPMD) implementation of a range encoder.

In some implementations, for a given value of the first encoded data set, the given value is compressed according to a 4-bit context relative to the position of the given value within the first encoded data set.

According to another innovative aspect of the present disclosure, another method for compressing nucleic acid sequence data is disclosed. In one aspect, the method can include obtaining, by one or more computers, nucleic acid sequence data representing (i) a read sequence comprising data that corresponds to a plurality of base calls generated by a nucleic acid sequencing device, and (ii) a plurality of quality scores, wherein each quality score of the plurality of quality scores indicates a likelihood that a particular base call of the read sequence was correctly generated by a nucleic acid sequencing device, determining, by one or more computers, a frequency of occurrence for each quality score group in the plurality of quality scores, wherein each quality score group comprises a subset of quality scores of the plurality of quality scores, for each particular quality score in a first subset of the plurality of quality scores: determining, by one or more computers, that the quality score is a member of a particular quality score group having a frequency of occurrence that satisfies a predetermined threshold, based on a determination that the quality score is a member of a particular quality score group having a frequency of occurrence that satisfies the predetermined threshold, generating, by one or more computers and using a predetermined group mapping, first data that is to be used as a single entry in a reduced sequence, wherein the first data that is to be used as the single entry in the reduced sequence represents the particular quality score group, and generating, by one or more computers, the reduced sequence by aggregating the generated first data for each of the particular quality score groups.

Other versions include corresponding systems, apparatus, and computer programs to perform the actions of methods defined by instructions encoded on computer readable storage devices.

These and other versions may optionally include one or more of the following features. For instance, in some implementations, the obtained data includes a FASTQ file.

In some implementations, each quality score in the plurality of quality scores is data representing an ASCII value for the quality score.

In some implementations, the method further comprises: for each particular quality score in a second subset of the plurality of quality scores: determining, by one or more computers, that the particular quality score in the second subset of the sequence of the quality scores is not a member of a particular quality score group having a frequency of occurrence that satisfies a predetermined threshold, and generating, by one or more computers and using a predetermined single mapping, second data that is to be used as a single entry in a reduced sequence, wherein the second data that is be used as the single entry in the reduced sequence represents the quality score that is not a member of a particular quality score group having a frequency of occurrence that satisfies the predetermined threshold, wherein the predetermined single mapping defines a one-to-one mapping between each of a plurality of single quality scores and a corresponding single entry.

In some implementations, generating, by one or more computers, the reduced sequence can include aggregating, by one or more computers, the generated first data for each of the particular quality score groups, and aggregating, by one or more computers, the generated second data for each of the quality scores that are not a member of a particular quality score group having a frequency of occurrence that satisfies the predetermined threshold.

In some implementations, the method can further include identifying, by one or more computers, a plurality of quality score groups in the plurality of quality scores.

In some implementations, the predetermined group mapping defines a one-to-one mapping between each of a plurality of different quality score groups and a corresponding single entry.

According to another innovative aspect of the present disclosure, another method for compressing nucleic acid sequence data is disclosed. In one aspect, the method can include obtaining, by one or more computers, nucleic acid sequence data representing (i) a read sequence comprising data that corresponds to a plurality of base calls generated by a nucleic acid sequencing device, and (ii) a plurality of quality scores, wherein each quality score of the plurality of quality scores indicates a likelihood that a particular base call of the read sequence was correctly identified by a nucleic acid sequencing device, determining, by one or more computers, a frequency of occurrence for each quality score group in the plurality of quality scores, wherein each quality score group comprises a subset of quality scores of the plurality of quality scores, for each particular quality score in a first subset of the plurality of quality scores: determining, by one or more computers, that the particular quality score in the first subset of the plurality of the quality scores is not a member of a particular quality score group having a frequency of occurrence that satisfies a predetermined threshold, and generating, by one or more computers and using a predetermined single mapping, first data that is to be used as a single entry in a reduced sequence, wherein the first data that is be used as the single entry in the reduced sequence represents the quality score that is not a member of a particular quality score group having a frequency of occurrence that satisfies the predetermined threshold, and generating, by one or more computers, the reduced sequence by aggregating the generated first data for each of the quality scores that are not a member of a particular quality score group having a frequency of occurrence that satisfies the predetermined threshold.

Other versions include corresponding systems, apparatus, and computer programs to perform the actions of methods defined by instructions encoded on computer readable storage devices.

These and other versions may optionally include one or more of the following features. For instance, in some implementations the obtained data includes a FASTQ file.

In some implementations, each quality score in the plurality of quality scores is data representing an ASCII value for the quality score.

In some implementations, method can further include for each particular quality score in a second subset of the plurality of quality scores: determining, by one or more computers, that the quality score is a member of a particular quality score group having a frequency of occurrence that satisfies a predetermined threshold, and based on a determination that the quality score is a member of a particular quality score group having a frequency of occurrence that satisfies the predetermined threshold, generating, by one or more computers and using a predetermined group mapping, second data that is to be used as a single entry in a reduced sequence, wherein the second data that is to be used as the single entry in the reduced sequence represents the particular quality score group, wherein the predetermined group mapping defines a one-to-one mapping between each of a plurality of different quality score groups and a corresponding single entry.

In some implementations, generating, by one or more computers, the reduced sequence can include aggregating, by one or more computers, the generated first data for each of the quality scores that are not a member of a particular quality score group having a frequency of occurrence that satisfies the predetermined threshold, and aggregating, by one or more computers, the generated second data for each of the particular quality score groups.

In some implementations, the method can further includes identifying, by one or more computers, a plurality of quality score groups in the plurality of quality scores.

In some implementations, the predetermined single mapping defines a one-to-one mapping between each of a plurality of single quality scores and a corresponding single entry.

These and other innovative aspects of the present disclosure are described herein below with reference to the detail description, the drawings, and the accompanying claims.

BRIEF DESCRIPTION OF THE DRAWINGS

FIG. 5 is a flow diagram illustrating an example of a process for decompressing a sequence of quality scores having a first data format.

Like reference numbers and designations in the various drawings indicate like elements.

DETAILED DESCRIPTION

Figure 1:
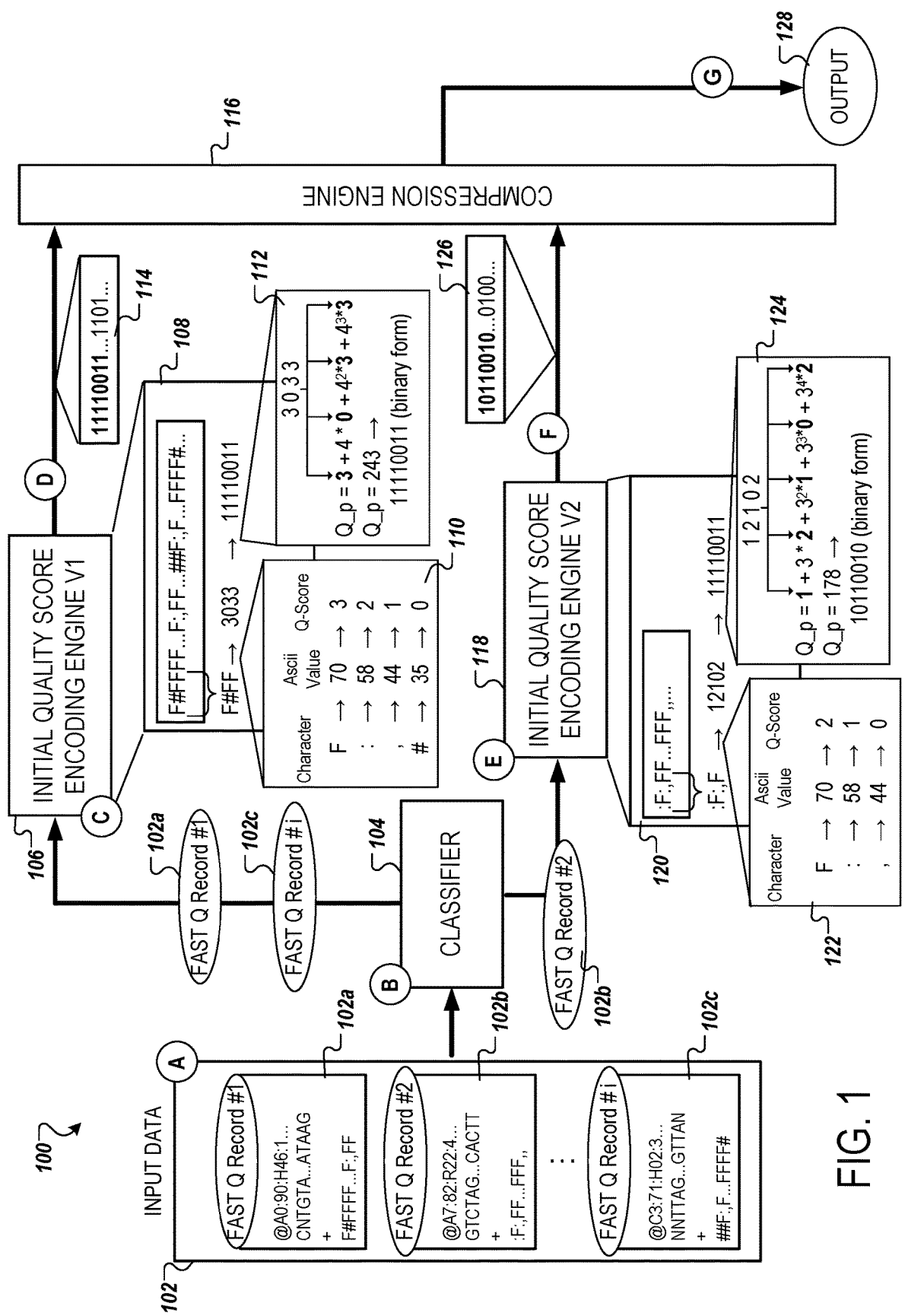
FIG. 1 is a diagram showing an example of a system for encoding, e.g., compressing, a sequence of quality scores having a first data format.

The present disclosure is directed towards methods, systems, and computer programs for the compression of data representing a sequence of quality scores for read sequences generated by a nucleic acid sequencing device. Each quality score in the sequence of quality scores provides an indication of a likelihood that a corresponding base in a read sequence was correctly sequenced by the nucleic acid sequencing device. The methods and systems disclosed herein enable faster compression speed and higher compression ratios when compared to conventional methods that do not utilize the techniques described herein. The faster compression speeds and higher compression ratios are achieved by performing pre-compression encoding steps to reduce the size of input data representing sequences of quality scores that are processed by a compression engine. Because the compression engine receives and processes a reduced size input representing sequences of quality scores, the compression engine can perform compression of the input data faster and achieve compressed files that are smaller in size relative to conventional methods. The compression methods of the present disclosure are thus able to achieve higher compression ratios than conventional systems, where the compression ratio is equal to the uncompressed file size divided by the compressed file size.

In general, the present disclosure describes systems and methods that execute an initial encoding stage on data representing a quality score sequence prior to inputting data representing the quality score sequence into a compression engine. The benefits of this approach can be described with respect to a particular example. In one or more first implementations, each quality score in the sequence of quality scores can be represented as an 8-bit (or one byte) ASCII value. In such first implementations described herein, the present disclosure can perform an initial encoding on such an 8-bit representation of a quality score in a sequence of quality scores to reduce the 8-bit representation of the quality score to a 2-bit representation or a 1.6 bit representation of the quality score, thus enabling 4 quality scores or 5 quality scores, respectively, to be encoded into a single byte. Such an initial encoding stage can thus significantly and predictably reduce the input data size to a compression engine by as much as one-fourth or one-fifth the size of the initial representation of the quality scores.

However, the present disclosure is not limited to reducing an 8-bit representation of a quality score to either a 2-bit representation of a quality score or a 1.6 bit representation of quality score for input to a compression engine. Rather, similar ratio reductions can be achieved with other sized representations of quality scores. These examples are being provided, in part, to highlight technological improvements achieved by the present disclosure.

Moreover, other second implementations of the present disclosure describe other initial stage encoding engines that perform operations on data representing a sequence of quality scores to generate a reduced sequence set for input into a compression engine. Such second implementations provide similar technological benefits as the implementations described above (e.g., faster compression speed and higher compression ratio compared with conventional methods). However, with an initial size reduction of the input data prior to its input into the compression engine that is variable and related to spontaneous grouping or non-grouping of quality scores, these second implementations though still resulting in faster compression speeds, lower compressed file sizes, and higher compression ratios than conventional methods, may ultimately have faster speeds and compression ratios that are less predictable than the first implementations of the present disclosure described above, which can have defined data sizes at each stage.

In general, the term "encoding," as used herein refers to a process(es) performed by one or more software engines, one or more hardware engines (e.g., processors), or a combination thereof, that includes receiving a first set of data and processing the first set of data to generate a second set of data that represents the first set of data in a different form. In some embodiments, the second set of data can be stored in less memory than the received first set of data. For example, one form of encoding data can include compressing data, e.g., with a compression engine into a smaller size than the size of the data prior to the compression.

FIG. 1 is a diagram showing an example of a system 100 for compressing a sequence of quality scores having a first data format. The first data format can assign "X" number of different quality scores to a corresponding base in a read sequence, where "X" is any positive integer less than a given threshold. The given threshold can be determined based on a number of unique quality scores that make using the system 100 depicted in FIG. 1 more effective or practical than other systems such as the system 300 depicted in FIG. 3. For example, the given threshold can be 8. If "X" is less than 8, the corresponding quality scores can be processed by the system 100. By way of a particular example, in some implementations, "X" can be equal to 4 indicating that the first data format can use any one of 4 different quality scores to indicate a likelihood that one or more base calls of a read sequence generated by a nucleic acid sequencing device is correct. In some implementations, the likelihood can include a probability that a sequencing error occurred at the one or more base calls corresponding to a quality score. In some embodiments, a sequencing error can include a base call made by a nucleic acid sequencing device for a particular location in a read sequence that is incorrect. For example, a sequencing device may determine a base call of Adenine represented by the letter A for a particular location in a read sequence when, in fact, the correct base call should have been Cytosine represented by the letter C. A low quality score for the given base call can indicate that such an error is more likely whereas a high quality score can indicate that such an error is less likely. A base call can include data, generated by a nucleic acid sequencing device, which represents a particular nucleotide of a read sequence.

The system 100 is configured to receive input data 102 from one or more data sources. In some implementations, the one or more data sources can include a nucleic acid sequencing device. The nucleic acid sequencing device can be a next-generation sequencing device such as a Novaseq® 6000, Nextseq® 2000, or the like. In other implementations, the one or more data sources can include one or more processors operating on computing devices such as a tablet computer, a desktop computer, one or more server computers, or a combination thereof. In some implementations, the input data 102 can be received from the one or more data sources via one or more networks. The one or more networks can include a wired Ethernet network, a wired optical network, a wireless network, a LAN, a WAN, a Wi-Fi network, a cellular network, the Internet, or any combination thereof. In some implementations, the input data 102 can be received from one or more data sources via a direct connection such as USB cable connection, a USB-C cable connection, or the like. In yet other implementations, the entire system 100 can be hosted within the one or more data sources. For example, in some implementations, the entire system 100 can be hosted by a nucleic acid sequencing device.

The system 100 can include an input engine that receives the input data 102. The input data 102 can include a plurality of records that each include data describing a read sequence comprising data that corresponds to a series of base calls as well as data describing quality scores for the series of nucleotides or bases. A base call can include data generated by a nucleic acid sequencer device that corresponds to or represents a nucleotide of a DNA fragment sequenced by the nucleic acid sequencer device. However, for purpose of the present disclosure, the terms base call and nucleotide can be used interchangeably throughout to refer to data generated by a nucleic acid sequencer that corresponds to a letter such as A, C, T, or G of read sequence. The meaning of such letters are described in more detail below.

In each record, each quality score in the sequence of quality scores can correspond to a particular nucleotide or base in a read sequence. For example, in the example of FIG. 1, the first quality scores "F" of the sequence of quality scores "F #FFFF . . . F;FF" corresponds to the first nucleotide or base in the read sequence "CNTGTA . . . ATAAG." In some implementations, the input data 102 can include one or more FASTQ files and each record of the plurality of records can include a portion of the FASTQ files, referred to herein as a FASTQ record. Each portion of the FASTQ file can include one read sequence and a corresponding sequence of quality scores for the read sequence.

Each read sequence can be previously generated by one or more nucleic acid sequencing devices from sequencing, by the one or more nucleic acid sequencer, a biological sample. The biological sample can include a nucleic acid sample of any living organism such as a human, an animal, or a plant. Each read sequence includes a string of letters from a defined vocabulary. For example, the smallest vocabulary can be represented by a set of five symbols: {A, C, G, T, N}. The letters A, C, G, and T represent the four types of nucleotides present in deoxyribonucleic acid (DNA), namely Adenine, Cytosine, Guanine, and Thymine. In ribonucleic acid (RNA), Thymine is replaced by Uracil (U). The letter "N" can be used, by the nucleic acid sequencing device to indicate that the sequencing device was not able to call any base at a particular location of the read sequence occupied by the "N," and so the real and correct nature of the position in the read sequence is undetermined. The use of letters A, C, G, and T or U is common, as these letters represent the first letter of each of the respective nucleotides. However, the present disclosure is not limited to the use of the letter "N" to represent a position in a generated read sequence that is undetermined. Instead, any letter or symbol can be used by a nucleic acid sequencing device to represent a location in a read sequence where the nucleic acid sequencing device is unable to accurately call a correct base. It is understood that, in the implementations described herein, the letter or symbol used to represent the unknown base is equivalent to the use of the letter "N."

Storing quality scores for bases of a read sequence can have many useful applications. However, given a sequenced genome for living organisms, such as a human, can include 3 billion+ bases and a corresponding 3+ billion corresponding quality scores. The data corresponding to the resulting sets of quality scores can be very large (e.g. multiple gigabytes to terabytes, depending on depth of sequencing) and can require compression in order to store, transmit, or archive the quality score information efficiently. Aspects of the present disclosure described with reference to FIG. 1 provide a multi-stage compression method that relies on an initial encoding engine to prepare an input data set for a compression engine. By initially encoding the data based on inherent properties of the input data 102 before a later stage use of a compression engine, the system 100 can achieve high compression ratios while maintaining fast compression speeds. The resulting compressed quality scores can have a reduced memory footprint that can reduce operating costs for related memory storage as well as increase processing speed when accessing or analyzing the resulting compressed quality scores. For purposes of the present disclosure, an "engine" can include one or more software modules, one or more hardware modules, or any combination thereof.

At stage A, a classifier engine 104 can obtain the input data 102 and route targeted or specific portions of the input data 102 to different initial quality score encoding engines based on attributes of the specific portions of the input data 102. Within the context of this disclosure, the process of obtaining refers to the process of receiving, retrieving, or otherwise acquiring. In some implementations, the classifier engine 104 can function as a decision engine that determines whether each particular portion of the input data 102 should be provided to initial quality score encoding engine V1 106 or an initial quality score encoding engine v2 118. After performing their respective initial encoding operations on portions of the input data 102 that they receive, each of the initial encoding engines V1, V2 can provide their respective encoded outputs 114, 126 as an input to the compression engine 116. The compression engine can process encoded outputs 114, 126 that it receives as inputs and can generate a final output 128 that is a compressed version of the input data 102.

In more detail at stage A of FIG. 1, the input data 102 obtained by the classifier engine 104 can include a first record 102a, a second record 102b, and an ith record 102c. In the example of FIG. 1, the first record 102a, the second record 102b, and the ith record 102c can be portions of a FASTQ file, which are also referred to herein as a FASTQ record. A FASTQ record can include a record header (e.g. "@A0:90:H46:1 . . . ") that identifies the FASTQ file from which the FASTQ record originated and distinguishes the FASTQ record from other FASTQ records. A FASTQ record can include data representing a read sequence generated by a nucleic acid sequencer. A FASTQ record can also include a sequence of quality scores that corresponds to the sequence of the FASTQ record. A FASTQ record can further include one or more delimiters in order to separate one or more data components, e.g., the record header, the quality score sequence, the sequence, or the like.

In the example of FIG. 1, the input data 102 is shown with three data records, however, any number of records may be included within the input data 102. The three data records are shown in subsequent processes in FIG. 1 but any number of records may be processed in a similar manner. At stage B, the classifier engine 104 can determine, based on one or more classification rules, classifications for each of the first record 102a, the second record 102b, and the ith record 102c of the input data 102. In some implementations, the classifications can be determined based on based calls of the read sequences in the respective FASTQ records.

In some implementations, for example, the classifier engine 104 can classify, or route, each FASTQ record to an initial quality score encoding engine V1, V2 based on whether the read sequence in the FASTQ record includes at least one "N" base. If it is determined that the read sequence of a FASTQ record includes at least one "N" base, then the FASTQ record can be routed to the initial quality score encoding engine V1 106. Alternatively, if it is determined that the read sequence of a FASTQ record does not include at least one "N" base, then the FASTQ record can be routed to the initial quality score encoding engine V2 118. However, this is just one example of a classification rule and it is considered that other types of classifier rules can be used in accordance with the present disclosure to classify and route FASTQ records between the initial quality score encoding engines V1, V2. In some implementations, the classifier engine 104 uses other elements of the input data to classify the input data. For example, instead of classifying based on the presence or absence of "N" bases, the classifier engine 104 can classify based on a percentage or determined portion of "N" bases or other bases. In addition, other base calls or corresponding data, e.g., quality scores, can be used by the classifier engine 104 to classify or route one or more FAST Q records or related data.

In the example of FIG. 1, the classifier engine 104 can determine, at stage B and based on the base calls of the respective read sequences of the first FASTQ record 102a and the ith FASTQ record 102c, that both the first FASTQ record 102a and the ith FASTQ record 102c include data representing a read sequence having at least one "N" base. Based on the determination that the first FASTQ record 102a and the ith FASTQ record 102c each have at least one "N" base, classifier engine 104 can route the first FASTQ record 102a and the ith FASTQ record 102c to the initial quality score encoding engine v1 106. In some implementations, the classifier engine 104 routes data corresponding to the first FASTQ record 102a and the ith FASTQ record 102c, for example, without sending one or more complete FASTQ record corresponding to the first FASTQ record 102a or the ith FASTQ record 102c. After routing data corresponding to the first FASTQ record 102a and the ith FASTQ record 102C to the initial quality score encoding engine v1 106, the execution of system 100 can continue at stage C.

At stage C, the initial quality score encoding engine v1 106 can obtain the respective quality score sequences of the first FASTQ record 102a and the ith FASTQ record 102c that correspond to the read sequence of the first FASTQ record 102a and the ith FASTQ record 102c, respectively. In this example, the quality score sequences received by the initial quality score encoding engine v1 106 can include 4 quality scores and each of the 4 quality scores are represented by an 8-bit ASCII value "F", ":", ",", and "#," with "#" representing the quality score for the "N" bases. However, in other implementations, there may be less than or more than 4 quality scores, with other characters or symbols that can be used to denote similar information.

The initial quality score encoding engine v1 106 can perform, at stage C, an initial encoding on the sequence of quality scores in the first record 102a. This initial encoding performed by the initial quality score encoding engine v1 106 can encode each quality score from the sequence of quality scores in the first FASTQ record 102a. This initial encoding can include encoding the 8-bit ASCII representation of each of the quality scores "F", ":", ",", or "#" into a 2-bit representation of each respective quality score. In some implementations, encoding of each 8-bit ASCII representation of each quality score of the quality score sequence of the first FASTQ record 102a can result in the initial quality score encoding engine 106 producing output data 114 that includes 4 quality scores per byte. This encoding ratio generated by the initial quality score encoding engine v1 106 reduces the size of input data records to the compression engine 116 by a factor of 4. In other implementations, other compression ratios may be realized by compressing greater or fewer quality scores, or quality scores of different data sizes, into one or more bits of information.

The initial quality score encoding engine v1 106 can continue to perform the initial encoding process on each FASTQ record that is routed to the initial quality score packing engine v1 106. For example, the initial quality score encoding engine v1 106 can receive the $i^{th}$ FASTQ record 102c and encode quality scores from the sequence of quality scores from an 8-bit ASCII value into a 2-bit representation of the quality scores. This process can continue until sequence of quality scores received by the initial quality score packing engine v1 have each been processed to generate their initial encoding into 2-bit quality scores.

In more detail, the initial quality score encoding engine v1 106 can perform the encoding of 8-bit quality scores into an output binary stream 114 of 2-bit quality scores by the executing the process shown in items 108, 110, and 112. The quality score encoding engine v1 106 can obtain a first 4 quality scores from a first record 102a. In some implementations, this may include the initial quality score encoding engine v1 106 obtaining the respective ASCII value of the quality scores. In other implementations, this may include obtaining other representations of the quality scores and mapping each respective quality score to a corresponding ASCII value as shown in 110. For example, the first 4 quality scores "F," "#," "F," and "F," can be mapped by the initial quality score encoding engine v1 106 to their corresponding ASCII values 70, 35, 70, and 70. Mappings for other quality scores using the first data format with "N" are shown in table 110. Then, the ASCII representation of the quality scores can be mapped to respective quality score category, where there is one category corresponding to each category of quality score. In this example, the quality score categories are represented by 0, 1, 2, and 3, as there are a range of 4 possible quality scores. However, there may be more (e.g., 0, 1, 2, 3, 4, 5, etc.) categories or less categories (e.g., 0, 1) based on the quality scoring system in use. While in this example, 0 corresponds to an unknown base and 3 corresponds to a high base quality score, the present disclosure is not limited to this implementation. Rather and for example, instead of integers, percentages out of 100, language-based score values, e.g., low, medium, and high, or other indicative values known in the art can be used to represent quality scores.

In the example of FIG. 1, the initial quality score encoding engine v1 106 can perform a calculation using the quality scores values 3, 0, 3, and 3 corresponding to the 4 ASCII based quality scores 'F', '#', 'F', and 'F'. The initial quality score encoding engine v1 106 can compute a quality encoded score using a formula such as $q_1+4*q_2+4^2*q_3+4^3*q_4$ where each of $q_1, q_2, q_3$, and $q_4$ represent quality score values. In the case of quality score values of 3, 0, 3, and 3, the formula can be evaluated as $3+4*0+4^2*3+4^3*3$ which equals 243 as shown in item 112. The initial quality score encoding engine v1 106 can generate a corresponding binary representation of these four quality scores by generating a binary representation of the number 243. This binary representation is 11110011, which can then be added to the output binary stream 114. This process can iteratively continue until each of the quality scores in the sequence of quality scores for the first FASTQ records 102a are initially encoded into the output binary stream 114.

After initial encoding of the sequence of quality scores of the first FASTQ record 102a, the initial quality score encoding engine v1 106 can continue performing the initial encoding process on each subsequent FASTQ record received. For example, the initial quality score encoding engine v1 106 can continue performing initial encoding of the ith FASTQ record 102c in the same manner described above with reference to the first FASTQ record 102a. The initial quality score encoding engine v1 106 can continue to obtain subsequent quality scores and perform initial encoding in a similar manner as the initial 4 quality scores shown in item 108.

At stage D, the initial quality score encoding engine v1 106 can send the output binary stream 114 to the compression engine 116. The compression engine 116 can then perform subsequent compression on the output binary stream 114 corresponding to a predetermined compression method. In general, any compression process can be employed by the compression engine 116 to further compress, or compress, the size of the output binary stream 114. For example, in some implementations, the compression engine 116 can perform compression using level 11 of the Zstandard (ZSTD) library. However, the present disclosure is not so limited. Instead, in some implementations, other compression methods may be used, including other levels of the ZSTD library as well as other compression libraries. In general, any compression method or combination of compression methods known in the art may be used.

In other instances, the classifier engine 104 can determine, by applying one or more classification rules, that a received FASTQ record includes a read sequence that does not include at least one "N." Based on a determination that the received FASTQ does not include at least one "N," the classifier engine 104 can route data corresponding to the second FASTQ record 102b to the initial quality score encoding engine v2 118.

Because the second FASTQ record 102b does not include any N, the range of potential quality scores can be the number of potential quality scores minus one. That is, if the classifier engine 104 determines the second FASTQ record to contain "X" potential quality scores, then the potential quality scores that may be processed at the initial quality score encoding engine v2 118 is "X"−1. In this implementation, the quality score sequence has only 3 distinct quality scores. Accordingly, in this example, only 3 distinct quality scores are to be separately compressed, in part, to realize a higher compression ratio.

In stage E, the initial quality score encoding engine v2 118 can obtain the quality score sequence of the second record 102b. The item 120 shows a subset of the quality scores of the quality score sequence the second record 102b. In more detail, the initial quality score encoding engine v2 1118 can perform the encoding of 8-bit quality scores into an output binary stream 126 of 1.6-bit quality scores by executing the process shown in items 120, 122, and 124. The initial quality score encoding engine v2 118 can obtain a determined number of quality scores from the second FASTQ record 102b, e.g., 5 quality scores. In some implementations, this may include the initial quality score encoding engine v2 118 merely obtaining the respective ASCII value of the quality scores. In other implementations, this may include obtaining another representation of the quality scores and mapping each respective quality score to a corresponding ASCII value as shown in 122. For example, the first 5 quality scores ":," "F," ":," ",," and "F," can be mapped by the initial quality score encoding engine v2 118 to their corresponding ASCII values 58, 70, 58, 44, and 70.

Then, the ASCII representation of the quality scores can be mapped to a respective quality score category, where there is one category corresponding to each category of quality score. In this example, the quality score categories are represented by 0, 1, and 2, as there is a range of 3 possible quality scores (i.e., X possible quality scores−1, because there is no "N" bases in the FASTQ records routed to the initial quality score encoding engine v2 118). In this example, the initial quality score encoding engine v2 118 can encode the 8-bit ASCII quality scores into a 1.6 bit quality score by representing the 8-bit ASCII quality score as a base-3 number. Base-3 is used because there are 3 unique categories of quality scores here.

However, the present disclosure is not limited to the example described above. Instead, in implementations where there are more quality score categories such as 8 total unique quality score categories, the initial quality score encoding engine v2 118 can obtain sequences with 7 unique quality score categories where the original 8 unique quality score categories include a quality score for an "N" base. In such an implementation, a base-7 number can be used to represent initial encodings of the initial quality score encoding engine v2 118.

Similar to item 112, item 124 shows a calculation performed by an initial encoding engine 118 related to a first set of quality scores. In this case, the initial quality score packing engine v2 118 computes a quality packed score using a formula such as $q_1+3*q_2+3^2*q_3+3^3*q_4+3^4*q_5$ where each of $q_1$, $q_2$, $q_3$, $q_4$, and $q_5$ represent quality score values. In the case of quality scores values 1, 2, 1, 0, and 2, the formula can be evaluated as $1+3*2+3*2+3^2*1+3^3*0+3^4*2$ which equals 178 as shown in item 124. The binary representation of 178, e.g., 10110010, can then be added to the output binary stream 126.

In the example of FIG. 1, the initial quality score packing engine v2 118 can encode 5 8-bit quality scores into a single ASCII character of 1 byte thereby compressing each quality score of the second record 102b by a factor of 5. In other implementations, other compression ratios may be realized by compressing greater or fewer quality scores, or quality scores of different data sizes, into one or more bits of information.

Similar to the initial quality score encoding engine v1 106, the initial quality score encoding engine v2 118 can obtain subsequent quality scores and perform encoding in a similar manner as the initial 5 quality scores shown in item 120. In stage F, the initial quality score encoding engine v2 118 can provide the output binary stream 126 as an input to the compression engine 116. The compression engine 116 can then perform subsequent compression on the output binary stream 126 corresponding to a predetermined compression method. For example, in some cases, the compression engine 116 performs compression based on the Prediction by Partial Matching (PPMD) implementation of a range encoder to compress the byte string. In some implementations, other compression methods known in the art may be used either instead of, or in addition to, a PPMD implementation. In general, the compression engine 116 can use any compression or combination of compression methods such as any compression method known in the art.

In some implementations, each symbol of the output binary stream 126 fed to the range encoder can be computed according to a 4 bit context, representing the number of highest quality score values in the preceding scores. For example, the 4 bit context can be computed as the total number of highest quality scores in the 30 preceding quality scores divided by 2. This particular 4 bit context formula can yield a value in the range of 0 to 15 that fits in the 4 bit context. By using a 4 bit context or other context-based encoding approaches, the system 100 can account for multiple adjacent instances of a particular quality score, e.g., the highest score 'F', which can be a good predictor of a subsequent score. In some implementations, larger or smaller contexts are used depending on memory, computation, or other requirements. For example, a larger context may yield a higher compression ratio but can require more memory and computation time.

In some implementations, other encoding engines can be used within the system 100. For example, in addition to the initial quality score encoding engine v1 106 and the initial quality score encoding engine v2 118, an implementation can include a third encoding engine based on specific criteria defined by the classifier engine 104. In some implementations, more than 3 engines may be used. In some implementations, the classifier engine 104 can determine a third set of records within the input data 102 that only uses 2 distinct quality scores. In this way, the system 100 can realize even greater compression ratios for the group with only 2 distinct quality scores.

Stages A through G are used for ease of description. Although the process performed by the system 100 may occur in the order indicated by stages A through G, in other implementations, the order of particular stages may be different. In some implementations, two or more stages may occur simultaneously.

Figure 2:
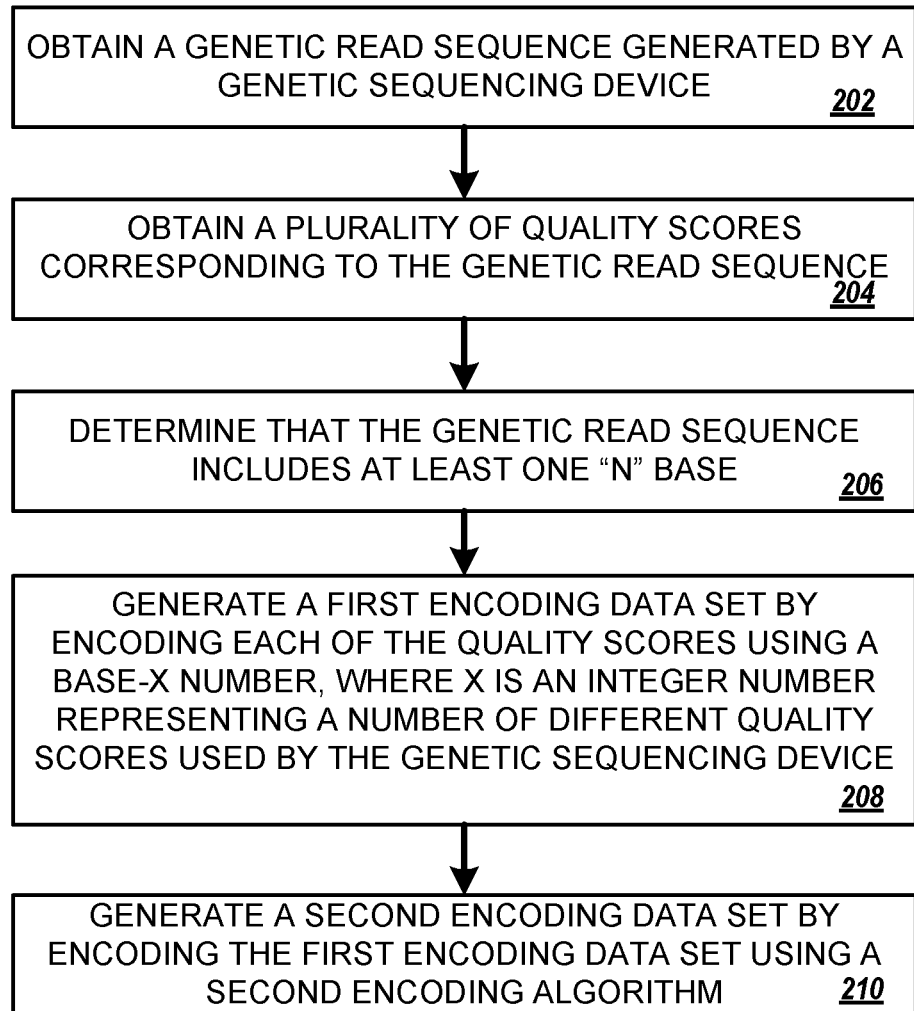
FIG. 2 is a flow diagram illustrating an example of a process for encoding, e.g., compressing, a sequence of quality scores having a first data format.

FIG. 2 is a flowchart illustrating an example of a process 200 for quality score compression based on a first input data format. The process 200 may be performed by one or more electronic systems, for example, the system 100 of FIG. 1.

The process 200 includes obtaining a genetic read sequence generated by a genetic sequencing device (202). For example, as shown in FIG. 1, the input data 102 is obtained and provided to the system 100. The input data 102 can include one or more records that each include data representing a read sequence comprising data that corresponds to a plurality of base calls generated by a nucleic acid sequencing device as well as data describing quality scores for the plurality of base calls. Each quality score of the quality scores corresponds to a particular base call of the read sequence.

In some implementations, characters are used to represent quality scores within the input data 102. For example, the first quality scores "F" of the sequence of quality scores "F #FFFF . . . F;FF" of the first FASTQ record 102a correspond to the first nucleotide or base (referred to hereinafter as "base") in the read sequence "CNTGTA . . . ATAAG" of the first FASTQ record 102a. In some implementations, the input data 102 can include one or more FASTQ files and each record of the plurality of records can include a portion of the FASTQ files, referred to herein as a FASTQ record. Each portion of the FASTQ file can include one read sequence and a corresponding sequence of quality scores for the read sequence.

The process 200 can include obtaining a plurality of quality scores corresponding to the genetic read sequence (204). For example, as shown in FIG. 1, the input data 102 includes the first record 102a, the second record 102b, and the ith record 102c. Each of the first record 102a, the second record 102b, and the ith record 102c include both a genetic sequence and a quality score sequence corresponding to the genetic sequence. For example, the first record 102a includes the genetic sequence "CNTGTA . . . ATAAG" and a corresponding quality score sequence of "F #FFFF . . . F:,FF" where each value of the quality score sequence indicates a likelihood of a sequencing error at a particular location of the corresponding genetic sequence.

The process 200 includes determining that the genetic read sequence includes at least one "N" base (206). For example, as shown in FIG. 1, the classifier engine 104 obtains the input data 102 that includes one or more genetic read sequences. The input data 102 includes the first record 102a. The first record 102a includes the genetic sequence "CNTGTA . . . ATAAG". The genetic sequence "CNTGTA . . . ATAAG" includes the base "N". The classifier engine 104 can determine that the genetic sequence "CNTGTA . . . ATAAG" of the first record 102a includes the base "N" and can route data corresponding to the first record 102a to the initial quality score encoding engine v1 106. Similarly, the classifier engine 104 can obtain the second record 102b. The second record 102b includes the genetic sequence "GTCTAG . . . CACTT" that does not include the base "N". The classifier engine 104 can determine that the genetic sequence "GTCTAG . . . CACTT" of the second record 102b does not include the base "N" and can route data corresponding to the second record 102b to the initial quality score encoding engine v2 118.

The process 200 includes generating a first encoded data set by encoding each of the quality scores using a base-x number, where x is an integer number representing a number of different quality scores used by the genetic sequencing device (208). For example, the initial quality score encoding engine v1 106 obtains the quality score sequence of the first record 102a. The quality score sequence of the first record 102a includes 4 unique quality scores: "F", ":", ",", and "#". Other suitable symbols or values may be used in other implementations. The initial quality score encoding engine v1 106 can then compute an integer based on a base-4 number. For example, as shown in item 108 of the FIG. 1, the initial quality score encoding engine v1 106 generates a value 3033 corresponding to the genetic quality scores "F #FF" based on the mapping shown in item 110. The initial quality score encoding engine v1 106 then generates an integer based on the value 3033 as if the value 3033 was written in a form of base-4 notation. As shown in item 112, the resulting integer equals 243 which can be written in 8 binary bits as "11110011." The equation used to generate the binary form of the group of quality scores, such as the quality scores "F #FF" can be constructed such that the integer value can be represented using 8 or fewer bits. For example, the equation used by the initial quality score encoding engine v1 106 can be constructed such that the integer value is less than 255.

For another example, the initial quality score encoding engine v2 118 obtains the quality score sequence of the second record 102b. The quality score sequence of the second record 102b, in contrast to the quality score sequence of the first record 102a, includes 3 unique quality scores: "F", ":", and ",". Other suitable symbols or values may be used in other implementations. The initial quality score encoding engine v2 118 can then compute an integer based on a base-3 number. Because there are fewer unique quality scores, the initial quality score encoding engine v2 118 can encode an additional quality score, e.g., 5 instead of 4, into 8 bits of binary. For example, as shown in item 124 of the FIG. 1, the initial quality score encoding engine v2 118 generates a value 12102 corresponding to the genetic quality scores ":F:,F" based on the mapping shown in item 122. The initial quality score encoding engine v2 118 then generates an integer based on the value 12102 as if the value 12102 was written in a form of base-3 notation. As shown in item 124, the resulting integer equals 178 which can be written in 8 binary bits as "10110010." The equation used to generate the binary form of the group of quality scores, such as the quality scores ":F:,F" can be constructed such that the integer value can be represented using 8 or fewer bits. For example, the equation used by the initial quality score encoding engine v2 118 can be constructed such that the integer value is less than 255.

The process 200 includes generating a second encoded data set by encoding the first encoded data set using a second encoding algorithm (210). For example, as shown in FIG. 1, the compression engine 116 generates the output 128 based on the input provided by the initial quality score encoding engine v1 106 or the initial quality score encoding engine v2 118. In some implementations, the compression engine 116 combines multiple outputs from different compression processes to generate the output 128. For example, both the initial quality score encoding engine v1 106 and the initial quality score encoding engine v2 118 can generate data for the compression engine 116 as shown in encoded outputs 114 and 126.

In some implementations, the compression engine 116 performs one or more types of compression based on the obtained data. For example, the compression process used to compress the output of the initial quality score encoding engine v1 106 can be different than the compression process used to compress the output of the initial quality score encoding engine v2 118. As discussed herein, compression of the encoded output 114 of the initial quality score encoding engine v1 106 can include zcompression using level 11 of the Zstandard (ZSTD) library or other forms of compression. Compression of the encoded output 126 of the initial quality score encoding engine v2 118 can include compression using the Prediction by Partial Matching (PPMD) implementation of a range encoder or other forms of compression. In some implementation, contexts around a given value of a sequence can be used to compress the given sequence. For example, a 4 bit context representing the number of highest quality score values in the preceding scores can be used by the compression engine 116. In some cases, multiple compression processes can be combined to produce compressed output.

Figure 3:
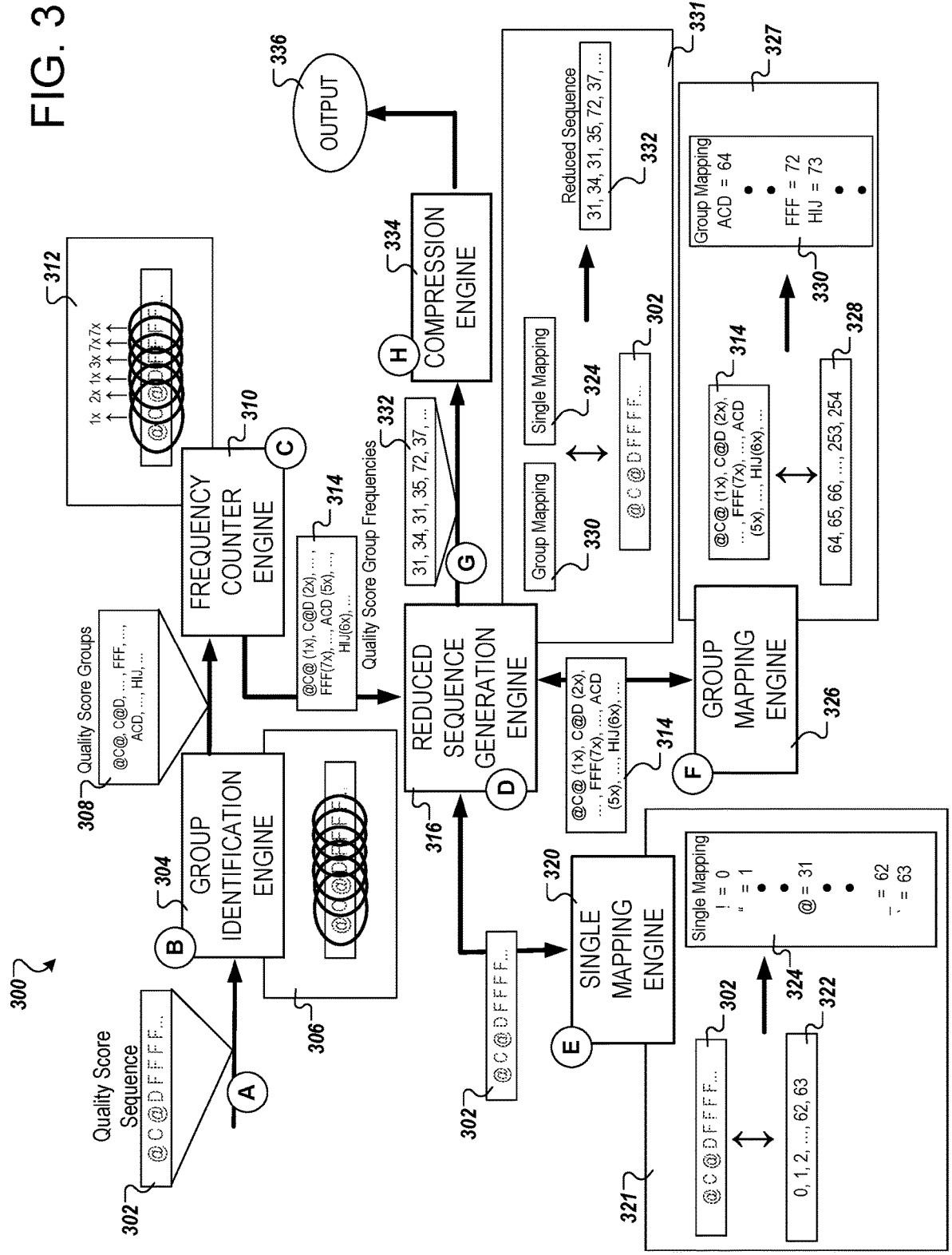
FIG. 3 is a diagram showing an example of a system for encoding, e.g., compressing, a sequence of quality scores having a second data format.

FIG. 3 is a diagram showing an example of a system for compressing a sequence of quality scores having a second data format. The system 300 includes a quality score sequence 302 that is formatted based on the Q40 data format. The quality score sequence 302 is processed by a group identification engine 304, a frequency counter engine 310, a reduced sequence generation engine 316, a single mapping engine 320, a group mapping engine 326, and a compression engine 334 to generate a reduced sequence 332 and subsequent output 336 that represents a compressed version of the quality score sequence 302.

In stage A of FIG. 3, the quality score sequence 302 is generated and sent to the group identification engine 304. In the example of FIG. 3, the quality score sequence 302 is generated by a sequencer that uses the Q40 data format to encode quality scores related to bases as discussed above. In general, any sequencer that uses greater than a threshold number of unique quality scores can compress resulting output data using a process performed by the system 300 shown in FIG. 3 or a similar process. For example, if a sequencer uses greater than 8 unique quality scores to encode quality scores corresponding to a genetic sequence, the sequencer can use the encoding and compression processes discussed in reference to FIG. 3.

In stage B, the group identification engine 304 obtains the quality score sequence 302 and generates one or more groups based on the quality score sequence 302 as shown in item 306. In this implementation, the group identification engine 304 groups adjacent quality scores in groups of 3. In other implementations, other numbers of quality scores may be included within one or more groups. As shown in item 316, the first group of 3 quality scores are the characters '@', 'C', and '@' corresponding to the characters of the quality score sequence 302. In the example of FIG. 3, each character of the quality score sequence 302 represents a quality score that indicates a likelihood of a sequencing error.

The group identification engine 304 generates quality score groups 308 and sends the quality score groups 308 to the frequency counter engine 310. In stage C, the frequency counter engine 310 obtains the quality score groups 308 and determines a number of occurrences for each of the groups within the quality score groups 308 as shown in item 312.

In some implementations, the group identification engine 304 and the frequency counter engine 310 work, at least partially, in parallel. For example, the group identification engine 304 can identify a single group based on the quality score sequence 302. The group identification engine 304 can then send the identified single group to the frequency counter engine 310. The frequency counter engine 310 can then determine the number of occurrences for the identified single group of quality scores. In some cases, generating a group from the quality score sequence 302 can include identifying one or more quality scores of the quality score sequence 302. In general, any process described within this specification may be threaded or run simultaneously with another process and the two or more processes may be run on one or more devices or instances of software.

The frequency counter engine 310 generates quality score group frequencies 314 and sends the quality score group frequencies 314 to the reduced sequence generation engine 316. A quality score group frequency 314 can include a number of occurrences of one or more quality scores in a quality score sequence 302. In stage D, the reduced sequence generation engine 316 can obtain the quality score group frequencies 314 and communicate with both the single mapping engine 320 and the group mapping engine 326. That is, the reduced sequence generation engine 316 can use the single mapping engine 320 at stage E to generate an entry in the reduced sequence 332 if a quality score of the quality score sequence 320 is not part of a group of quality scores having more than a threshold number of quality scores. Alternatively, the reduced sequence generation engine 316 can use the group mapping engine 326 at stage F if a quality score of the quality score sequence 320 is part of a group of quality scores having more than a threshold number of quality scores. For purposes of this disclosure, an "entry" or "single entry" of the reduced sequence 332 can include a single value such as "72" in reduced sequence 332 that was used to replace a single quality score or group of quality scores.

For purposes of this specification, one can determine whether a group of quality scores has more than threshold number of quality scores by using positive or negative representations of a threshold number of quality scores and a number of quality scores in a group. Accordingly, it is consistent with this specification to determine whether a number of quality scores in a group of quality scores "satisfies" a threshold and not merely whether the number of quality scores is more than a threshold. This is because such a relationship can be described as a group of quality scores having 4 quality scores exceeding a threshold of 3 quality scores or a group of quality scores having negative 4 quality scores is not greater than a threshold of negative 3 quality scores. In either case, a group of quality scores has more than 3 quality scores regardless of how the threshold is implemented.

For ease of explanation, this specification now describes processes of the single mapping engine 320 prior to describing the processes of the group mapping engine 326. However, simultaneous processing and other similar methods may be used such that the single mapping engine 320 need not complete single mapping processes prior to the group mapping engine 326 completing group mapping processes. Instead, whether the reduced sequence generation engine 316 calls the single mapping engine 320 or the group mapping engine 326 will be determined based on a particular quality score of the sequence of quality scores 302 being processed by the reduced sequence generation engine 326.

In stage E, the single mapping engine 320 obtains the quality score sequence 302. The single mapping engine 320 uses the quality score sequence 302 and a single mapping character list 322 to generate a predetermined single mapping 324, as shown in item 321. In the example of FIG. 3, the single mapping character list 322 includes the integer values 0 to 63. The ASCII values of the quality score sequence 302 include values 33 to 96. In this way, each value of the quality score sequence 302 can be mapped to a particular value between 0 and 63. For example, the '@' character of the quality score sequence 302 corresponding to the ASCII value 64 can be mapped to the integer value 31. Similarly, the 'A' character in a given quality score sequence corresponding to the ASCII value 65 can be mapped to the integer value 33, and so forth.

As shown in the predetermined single mapping 324, the ASCII character '!' corresponding to a value of 33 is mapped to a value of 0 that is between 0 and 63. The ASCII character '"' corresponding to a value of 34 is mapped to a value of 1. Similarly, the ASCII character '_' corresponding to a value of 95 is mapped to a value of 62 and the ASCII character '`' corresponding to a value of 96 is mapped to a value of 63. Other mappings not shown in the predetermined single mapping 324 can also be generated by the single mapping engine 320.

In other implementations, other mappings may be used. For example, instead of 0 to 63, smaller or larger ranges can be used in which the values of the quality score sequence 302, such as ASCII values from 33 to 96, are mapped to values between 33 and 96. Other mappings, such as mappings generated by the group mapping engine 326 may occupy value ranges other than the values between 33 and 96. In some implementations, the number of unique quality scores of the quality score sequence 302 is used to determine the range in which to map the quality scores of the quality score sequence 302. For example, if the quality score sequence 302 includes 63 unique quality scores, the range in which to map the quality scores of the quality score sequence 302 can include 63 values. In some implementations, other ranges are used. For example, if the quality score sequence 302 includes a first number of unique quality scores, a range can be computed, e.g., by the single mapping engine 320, to include the first number of unique quality scores divided by 2 or other calculation result based on the first number of unique quality scores. In some implementations, subsequent operations are applied to a processing result used to determine a mapping range. For example, if the first number of unique quality scores is odd and a first operation applied to the first number of unique quality scores is division by the integer 2, a second operation can include rounding a corresponding processing result up or down depending on the implementation.

In stage F, the group mapping engine 326 obtains the quality score group frequencies 314. The group mapping engine 326 uses the quality score group frequencies 314 or other data related to the quality score sequence 302 together with a group mapping character list 328 to generate a predetermined group mapping 330, as shown in item 327. In the example of FIG. 3, the group mapping character list 328 includes the integer values 64 to 245 corresponding to the 190 most frequently occurring groups. In some implementations, more or fewer groups may be mapped by the group mapping engine 326. For example, instead of generating the predetermined group mapping 330 that includes the 190 most frequently occurring groups, the group mapping engine 326 can generate a mapping that includes the 200, 230, 185 or any other number of most frequently occurring groups. The ASCII values corresponding to quality score group frequencies 314 include values 33 to 96. The group mapping engine 326 can, based on the quality score group frequencies 314 determine a portion of the groups for mapping. For example, the group mapping engine 326 can determine a certain number of the most frequently occurring groups, (e.g., 190 most frequently occurring groups) and assign each group of the most frequently occurring groups a value, e.g., an integer value from 64 to 254.

As shown in the predetermined group mapping 330, in the example of FIG. 3, the quality score group represented by the characters 'ACD' is mapped to the value 64. The quality score group represented by the characters 'FFF' is mapped to the value 72. The quality score group represented by the characters 'HIJ' is mapped to the value 73. Other mappings not shown in the predetermined group mapping 330 can also be generated by the group mapping engine 326.

In other implementations, other mappings may be used. For example, instead of 64 to 254, smaller or larger ranges can be used in which the groups within the quality score group frequencies 314 are mapped. For example, groups within the quality score group frequencies 314 can be mapped to values between 0 and 255. Other mappings, such as mappings generated by the single mapping engine 320 may occupy values other than the values used for group mappings between 0 and 255.

The reduced sequence generation engine 316 uses the group mapping engine 326 and the single mapping engine 320 to process the quality score sequence 302 in order to generate the reduced sequence 332. The data derived from the quality score sequence 302 can include the quality score sequence 332 itself. Alternatively, the data derived from the quality score sequence 302 can include data output by the frequency counter engine 310. The data output by the frequency counter engine 310 can include quality score group frequencies 314. The reduced sequence 332 is a combination of the values from the predetermined single mapping 324 and the predetermined group mapping 330.

The reduced sequence generation engine 316 can process the quality score sequence 302, the quality score group frequencies, or both, and determine whether to use the single mapping engine 320 or the group mapping engine 326 to generate an entry in the reduced sequence 332. Occurrences of groups within the quality score sequence 302 that belong to a group within the predetermined group mapping 330 are replaced with the value from the predetermined group mapping 330. For example, occurrences of an 'A' quality score followed by a 'C' quality score followed by a 'D' quality score are replaced by the value 64 in the reduced sequence 332.

For quality scores that are not a member of one of the groups of the predetermined group mapping 330, the predetermined single mapping 324 is used. For example, the first value of the quality score sequence 302 is the character '@' corresponding to the ASCII value 64. The character '@', as it appears within the quality score sequence 302, is not a member of a group within the predetermined group mapping 330. The character '@' is then mapped based on the predetermined single mapping 324. The mapping for '@' based on the predetermined single mapping 324 is the value 31. The reduced sequence generation engine 316 adds the value 31 corresponding to the position of '@' within the reduced sequence 332.

In stage G, the reduced sequence generation engine 316 generates the reduced sequence 332 using the predetermined group mapping 330, the predetermined single mapping 324, and the data derived from the quality score sequence 302 as described above and as shown in item 331. The reduced sequence generation engine 316 sends the reduced sequence 332 to the compression engine 334.

In stage H, the compression engine 334 performs subsequent compression on the reduced sequence 332 corresponding to a predetermined compression method. For example, in some cases, the compression engine 334 performs compression based on the Prediction by Partial Matching (PPMD) implementation of a range encoder to compress the reduced sequence 332. In some implementations, other compression methods known in the art may be used either instead of, or in addition to, a PPMD implementation. In general, the compression engine 334 can use any compression or combination of compression methods such any compression method known in the art. The compression engine 334 generates the output 336 based on the reduced sequence 332 as an input to the compression method used by the compression engine 334. The output 336 represents a compressed version of the quality score sequence 302.

In some implementations, each value of the reduced sequence 332 fed to the compression engine 334 is compressed according to a 1 byte context. For example, for a given value of the reduced sequence 332, the previous value in the reduced sequence 332 can be used as context in order to compress the given value of the reduced sequence 332. The 1 byte context can be used to compress the reduced sequence 332 according to the PPMD implementation of a range encoder or another compression or encoding method. A larger or smaller context can be used in order to balance speed, the resulting compression output, or other parameters. In some cases, the resulting compression ratio for the output 336 can be greater or equal to 2 bits per quality score. For example, 4 or more quality scores can be compressed into 1 byte or 8 bits of memory space. In general, the output 336, similar to the output 128 of FIG. 1, can be used in any further processes or can be stored depending on implementation.

Stages A through H are used for ease of description. Although the process performed by the system 300 may occur in the order indicated by stages A through H, in other implementations, the order of particular stages may be different. In some implementations, two or more stages may occur simultaneously.

Figure 4:
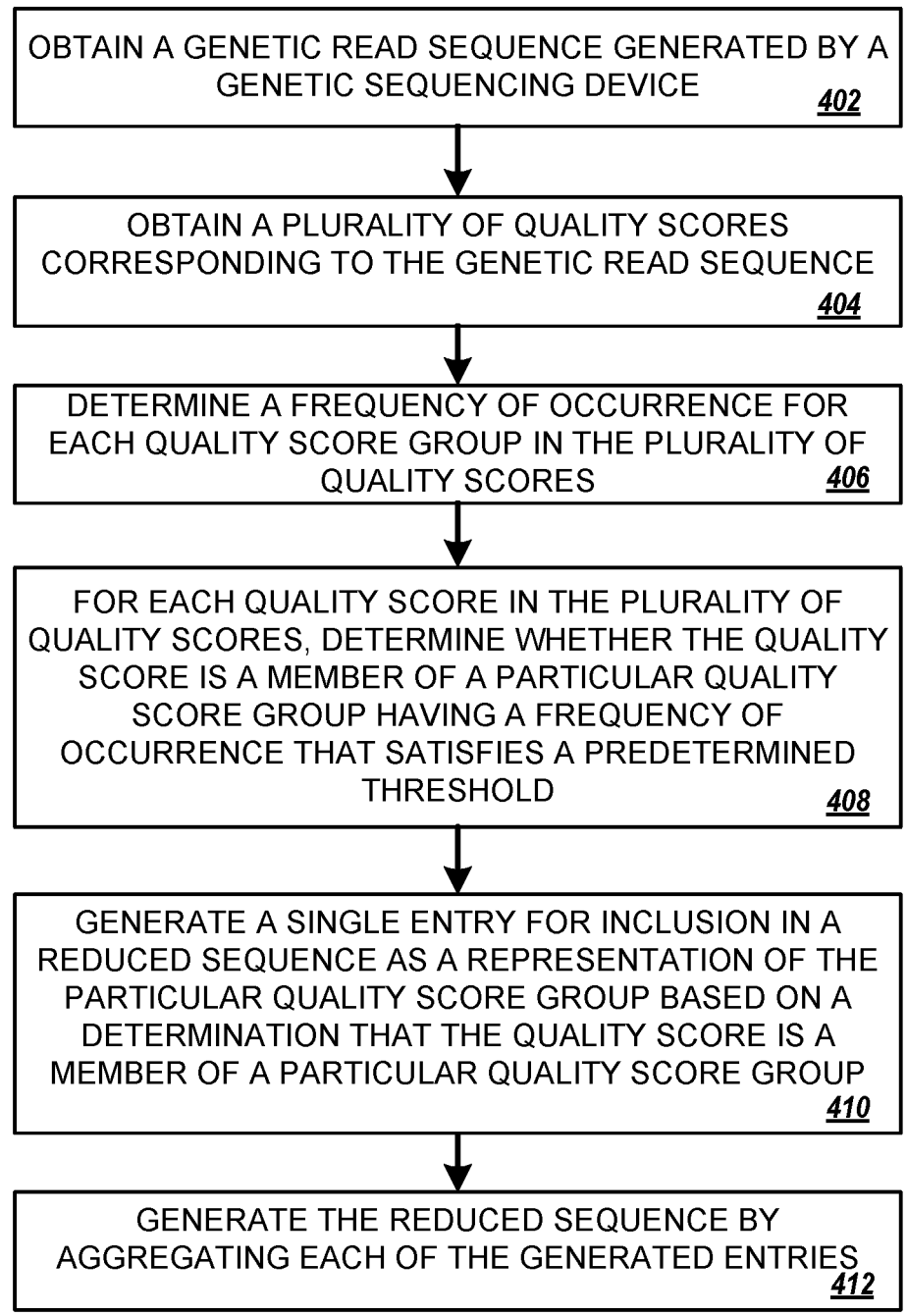
FIG. 4 is a flow diagram illustrating an example of a process for encoding, e.g., compressing, a sequence of quality scores having a second data format.

FIG. 4 is a flow diagram illustrating an example of a process for compressing a sequence of quality scores having a second data format. The process 400 may be performed by one or more electronic systems, for example, the system 300 of FIG. 3.

The process 400 includes obtaining a genetic read sequence generated by a genetic sequencing device (402) and obtaining a plurality of quality scores corresponding to the genetic read sequence (404). For example, as shown in FIG. 3, the quality score sequence 302 is generated by a sequencer based on a genetic data sequence and sent to the group identification engine 304. In the example of FIG. 3, the quality score sequence 302 is generated by sequencer that uses the Q40 data format to encode quality scores related to bases as discussed above. In general, any sequencer that uses greater than a threshold number of unique quality scores can compress resulting output data using a process performed by the system 300 shown in FIG. 3 or a similar process. For example, if a sequencer uses greater than 8 unique quality scores to encode quality scores corresponding to a genetic sequence, the sequencer can use the encoding and compression processes discussed in reference to FIG. 3.

The process 400 includes determining a frequency of occurrence for each quality score group in the plurality of quality scores (406). For example, as shown in FIG. 3, the group identification engine 304 obtains the quality score sequence 302 and generates a number of quality score groups based on the plurality of quality scores within the quality score sequence 302. In some implementations, the groups of quality scores include quality scores that are adjacent to one another within the quality score sequence 302. For example, if the quality score sequence 302 includes the quality scores, "@C @D F F F F . . . ", a group determined by the group identification engine 304 can include the quality scores "@C @" in implementations where 3 quality scores are used to generate a group.

In some implementations, the group identification engine 304 sends one or more groups to the frequency counter engine 310 and the frequency counter engine 310 determines the frequency of occurrence of each quality score group. For example, the frequency counter engine 310 can determine, for each group determined by the group identification engine 304, how may occurrences of the group are present within the quality score sequence 302. In the example, of FIG. 3, quality scores of the quality score sequence 302 are grouped into groups of 3. However, in other implementations, other numbers of quality scores may be used. For example, the group identification engine 304 can determine groups of 4 quality scores, 2 quality scores, or any other number of quality scores to generate a quality score group.

The process 400 includes, for each quality score in the plurality of quality scores, determining whether the quality score is a member of a particular quality score group having a frequency of occurrence that satisfies a predetermined threshold (408). For example, as shown in FIG. 3, the reduced sequence generation engine 316, the single mapping engine 320, and the group mapping engine 326 generate the reduced sequence 332 based on the predetermined single mapping 324 and the predetermined group mapping 330. For each quality score in the reduced sequence 332, the reduced sequence generation engine 316 determines if the quality score is a member of a group included in the predetermined group mapping 330. If the quality score is a member of a group included in the predetermined group mapping 330, the quality score, along with other quality scores of the group, are encoded as a single entry in the reduced sequence 332.

In some implementations, each group of the predetermined group mapping 330 satisfies a predetermined threshold. For example, each group of the predetermined group mapping 330 can occur within the quality score sequence 302 a predetermined number of times to be included in the group mapping. Each group of the predetermined group mapping 330 can belong to a predetermined number of groups that occur more frequently than other groups within the quality score sequence 302. In the example of FIG. 3, the predetermined group mapping 330 includes the 190 most frequently occurring quality score groups. A threshold can then be defined as the number of occurrences corresponding to the $191^{st}$ most frequently occurring quality score group, the $190^{th}$ most frequently occurring quality score group, among others depending on implementation. The 190 most frequently occurring quality score groups of the predetermined group mapping 330 then all satisfy this threshold.

In some implementations, a different amount of quality score groups can be used to generate the predetermined group mapping 330. For example, a number of groups of the predetermined group mapping 330 can be determined based on the number of quality scores used by a sequencer. The mapping can then be generated to satisfy an optimization process. For example, an optimization process can include maximizing the number of groups that are encoded as a single value and minimizing the number of quality scores that do not belong to a quality score group of the predetermined group mapping 330 and that are encoded as a single value. Parameters to optimize can include the number of groups to include in a group mapping such as the predetermined group mapping 330 of FIG. 3 as well as the number of quality scores that are used to generate one or more groups within the predetermined group mapping 330. The number of quality scores in a single mapping, such as the predetermined single mapping 324 of FIG. 3 can correspond to the number of unique quality scores used by a sequencer to represent quality scores corresponding to a genetic sequence read.

In some implementations, quality scores groups are based on adjacent quality scores appearing together within a quality score sequence. For example, the quality score sequence 302, represented as "@C @D F F F F . . . ", includes the group of adjacent quality scores "FFF". The group of adjacent quality scores "FFF" are included in the predetermined group mapping 330. According to the predetermined group mapping 330, the group of adjacent quality scores "FFF" are to be encoded by the reduced sequence generation engine 316 as the single value 72. Of course, in other implementations, other values may be used for mapping or encoding purposes.

In some implementations, scores that are not members of quality score groups are mapped as a single entry within a reduced sequence. For example, in an implementation that uses 3 quality scores to generate a group of quality scores, the first value, "@", of the quality score sequence 302, represented as "@C @D F F F F . . . ", is not a member of a particular quality score group. As such, the first value, "@", is encoded in the reduced sequence 332 as a single value 31 according to the predetermined single mapping 324. In the example of FIG. 3, the predetermined single mapping 324 is a one to one match of the values used to represent quality scores in the quality score sequence 302 and the new range of the same length such that any quality score not part of a group within the predetermined group mapping 330 is encoded in the reduced sequence 332 as the original value plus or minus a shifting value used to generate the predetermined single mapping 324. For example, in FIG. 3, the single values corresponding to quality scores that are not members of a quality score group are shifted by a value of 33. The shifting can be used to generate a continuous range of values devoted to either group mappings or single mappings.

The process 400 includes generating a single entry for inclusion in a reduced sequence as a representation of the particular quality score group based on a determination that the quality score is a member of a particular quality score group (410). For example, the reduced sequence generation engine 316 can determine that the quality score sequence 302, represented as "@C @D F F F F . . . ", includes the group of quality scores "FFF". The group of quality scores "FFF" are included in the predetermined group mapping 330. According to the predetermined group mapping 330, the group of adjacent quality scores "FFF" are to be encoded by the reduced sequence generation engine 316 as the single value 72. However, the present disclosure is not limited to replacing groups of quality scores with a single entry or value. In other implementations, a single quality score can be replaced with a single entry or value using a predetermined single mapping. Such single quality score replacements can be beneficial because a single entry or value can be selected to represent the single quality score that has a smaller bit-size than the single quality score.

The process 400 includes generating the reduced sequence by aggregating each of the generated entries (412). For example, the reduced sequence generation engine 316 can aggregate the first encoded value of 31 corresponding to the quality score "@" of the quality score sequence 302, represented as "@C @D F F F F . . . ", the second encoded value of 34 corresponding to the quality score "C", the third encoded value of 31 corresponding to the quality score "@", the further encoded value of 35 corresponding to the quality score "D", and the fifth encoded value of 72 corresponding to the quality score group "FFF". The reduced sequence generation engine 316 can generate subsequent encoded values based on subsequent values of the quality score sequence 302. The reduced sequence generation engine 316 can continue until all values of the quality score sequence 302 have been represented within the reduced sequence 332.

In some implementations, further compression steps are performed based on the reduced sequence 332. For example, as shown in FIG. 3, the reduced sequence 332 can be sent to the compression engine 334. The compression engine 334 can then perform one or more compression processes on the reduced sequence 332 to generate the output 336. Similar to the process depicted in FIG. 1, the first encoding represented by the reduced sequence 332 that is generated before subsequent compression steps performed by the compression engine 334 can be advantageous in improving the resulting compression of the output 336. The form of the reduced sequence 332 can be such that the compression engine 334 can compress the data more quickly or effectively than the original quality score sequence 302. For example, the reduced sequence 332 can be a compressed version of the quality score sequence 302 and the duration or quality of compression performed by the compression engine 334 can be dependent upon the size of the input. In this way, the initial encoding steps to generate the reduced sequence 332 can decrease the time it takes to compress and increase the quality of compression achieved by the compression engine 334.

FIG. 5 is a flow diagram illustrating an example of a process 500 for decompressing a sequence of quality scores having a first data format. The process 500 can be performed by one or more electronic systems, for example, the system 100 of FIG. 1.

The process 500 includes obtaining a first encoded data set generated by encoding each of a plurality of quality scores using a base-x number, where x is an integer number representing a number of different quality scores used by the genetic sequencing device (502). For example, a decoding engine can obtain the binary output 114 or the binary output 126.

The process 500 includes generating a first decoded data set using the base-x number (504). For example, similar to the processes shown in items 108 and 120, the first encoded data set can be decoded based on the base-x number used for encoded where x is an integer corresponding to the number of unique quality scores present in the plurality of quality scores. In some implementations, the integer value of the binary representation of the first decoded data can be iteratively divided by x of the base-x number to generate the base-x number.

The process 500 includes ordering the first decoded data set within one or more other decoded data sets (506). In some implementations, an ordering engine can obtain the decoded data set and one or more other decoded data sets and order the first decoded data based on the first encoded data set. For example, the ordering engine can determine, a portion of the first encoded data set that is then decoded to generate the first decoded data set. The ordering engine can also determine portions of the first encoded data set that are decoded to generate the one or more other decoded data sets. Based on the original location of the first decoded data set and the one or more other decoded data sets within the first encoded data set, the ordering engine can order the first decoded data set within one or more other decoded data sets.

The process 500 includes generating an aggregate decoded data set based on the first decoded data set and the one or more other decoded data sets (508). For example, based on the ordering of the first decoded data set within one or more other decoded data sets, an aggregate decoded data set engine can generate the aggregate decoded data set that includes the first decoded data set and the one or more other decoded data sets. The aggregate decoded data set can include data similar to the data used to generate the first encoded data set. The aggregate decoded data set can be used in other processes or operations depending on implementation.

Figure 6:
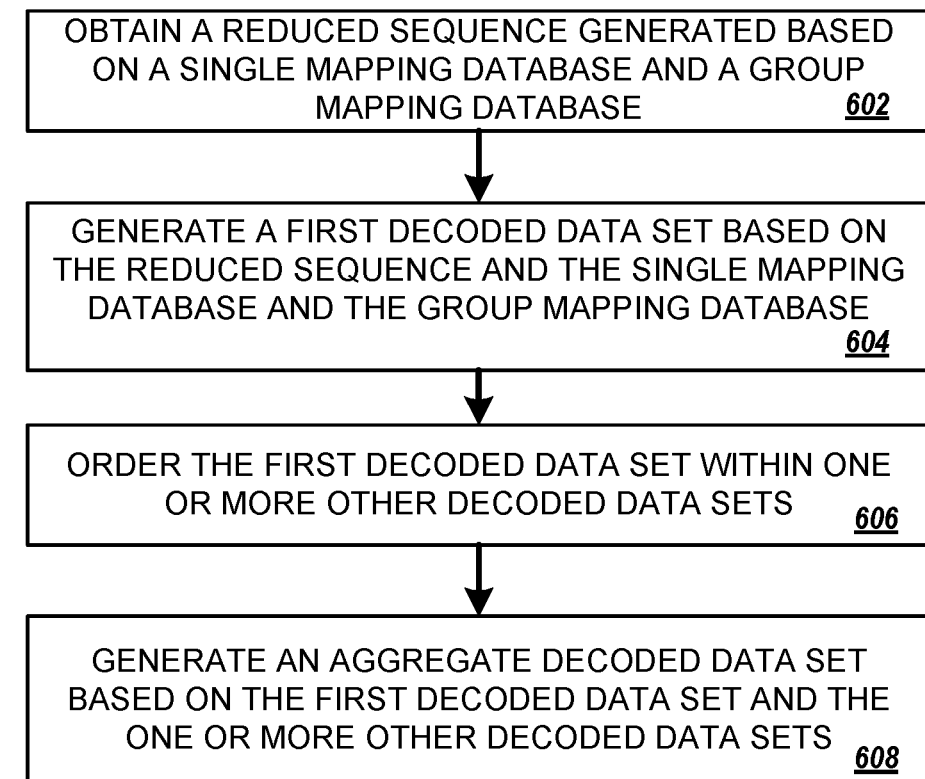
FIG. 6 is a flow diagram illustrating an example of a process for decompressing a sequence of quality scores having a second data format.

FIG. 6 is a flow diagram illustrating an example of a process 600 for decompressing a sequence of quality scores having a second data format. The process 600 may be performed by one or more electronic systems, for example, the system 300 of FIG. 3.

The process 600 includes obtaining a reduced sequence generated based on a single mapping database and a group mapping database (602). For example, a decoding engine can obtain the reduced sequence 332 or other related data from the system 300 or other system. The process shown corresponding to the reduced sequence generation engine 316 can then be performed in reverse to generate the quality score sequence 302.

The process 600 includes generating a first decoded data set based on the reduced sequence and the single mapping database and the group mapping database (604). As discussed above, the decoding engine can perform operations similar to the reduced sequence generation engine 316 but in a reversed order to generate the quality score sequence 302. For example, the decoding engine can obtain the reduced sequence 332 and use the predetermined group mapping 330 and the predetermined single mapping 324 to decode the reduced sequence 332 and generate the first decoded data set corresponding to at least a portion of the quality score sequence 302.

The process 600 includes ordering the first decoded data set within one or more other decoded data sets (606). For example, the decoding engine can decode a first portion of the reduced sequence 332 and determine a first order corresponding to the first portion of the reduced sequence 332. In some implementations, the order of the reduced sequence 332 can be used to determine the order of the first decoded data set and the one or more other decoded data sets. For example, the first decoded data set can correspond to a first portion of the reduced sequence 332. As a result, the first decoded data set can be ordered at the beginning of a final aggregated decoded data set. Subsequent one or more other decoded data sets can then be ordered based on the order of the data corresponding to the reduced sequence 332 used to generate the one or more other decoded data sets.

The process 600 includes generating an aggregate decoded data set based on the first decoded data set and the one or more other decoded data sets (608). For example, an aggregate decoded data set engine can be used to generate the aggregate decoded data set based on ordering the first decoded data set within the one or more other decoded data sets as discussed above. The aggregate decoded data set can include data similar to the data used to generate the reduced sequence such as the reduced sequence 332. The aggregate decoded data set can be used in other processes or operations depending on implementation.

Figure 7:
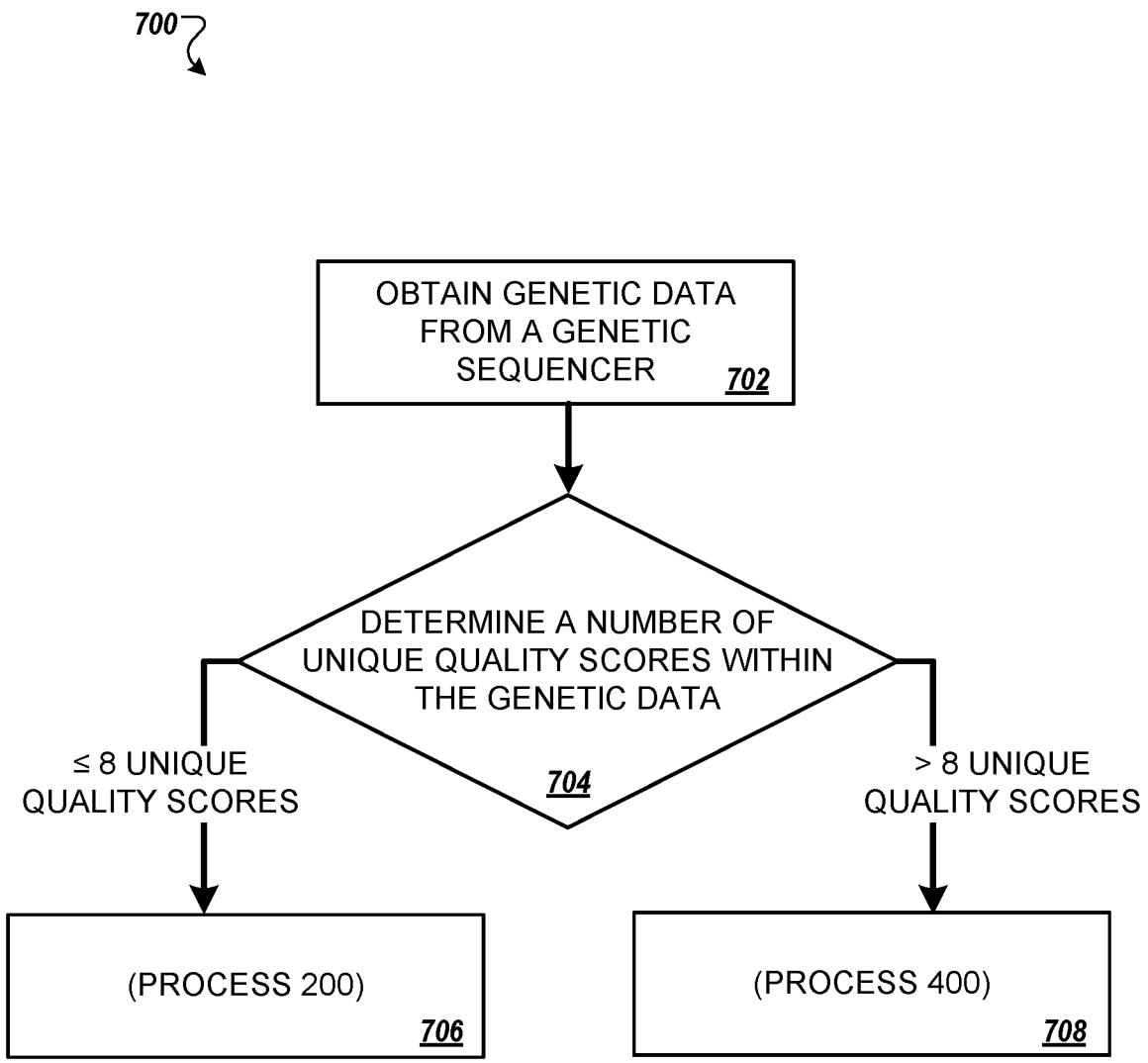
FIG. 7 is a flow diagram illustrating an example of a process for determining a compression method of quality scores.

FIG. 7 is a flow diagram illustrating an example of a process 700 for determining a compression method of quality scores. The process 700 may be performed by one or more electronic systems, for example, the system 300 of FIG. 3 or the system 100 of FIG. 1.

The process 700 includes obtaining genetic data from a genetic sequencer (702). The various forms of genetic sequencers will be known to one skilled in the art. For example, a decision engine can obtain genetic data corresponding to one or more quality scores generated by the given genetic sequencer.

The process 700 includes determining a number of unique quality scores within the genetic data (704). For example, depending on the type, model, or particular software of the given sequencer, quality scores for base calls may be expressed by one or more symbols or values. The number of unique symbols or values used to represent one or more quality scores can then be used to determine which compression method to use for the quality scores of the genetic data.

The process 700 includes a first decision path corresponding to a determination that 8 or fewer unique quality scores are present within the genetic data obtained from the genetic sequencer and a second decision path corresponding to a determination that more than 8 unique quality scores are present within the genetic data obtained from the genetic sequencer. If 8 or fewer unique quality scores are present within the genetic data, a process corresponding to the process 200 described in FIG. 2 may be performed to compress the quality scores of the genetic data. If more than 8 unique quality scores are present within the genetic data, a process corresponding to the process 400 described in FIG. 4 may be performed to compress the quality scores of the genetic data.

In some implementations, other thresholds are used to determine what compression method to use. For example, instead of 8 unique quality scores, a system may determine that 7, 9, or 10 unique quality scores are necessary to pursue a process corresponding to the process 400 described in FIG. 4. In general, a system may use any suitable thresholds or decision modeling to determine which of a plurality of different compression methods to use to compress a given set of data such as a given set of quality scores.

The genomic data referred to in the present disclosure, e.g., the input data 102, and the like, can include, for example, and not as a limitation, nucleotide sequences, Deoxyribonucleic acid (DNA) sequences, Ribonucleic acid (RNA), and amino acid sequences. Although the description herein is in considerable detail with respect to genomic information in the form of a nucleotide sequence, it will be understood that the ordered data sequence of this specification can be implemented for other genomic data as well, albeit with a few variations, as will be understood by a person skilled in the art.

Figure 8:
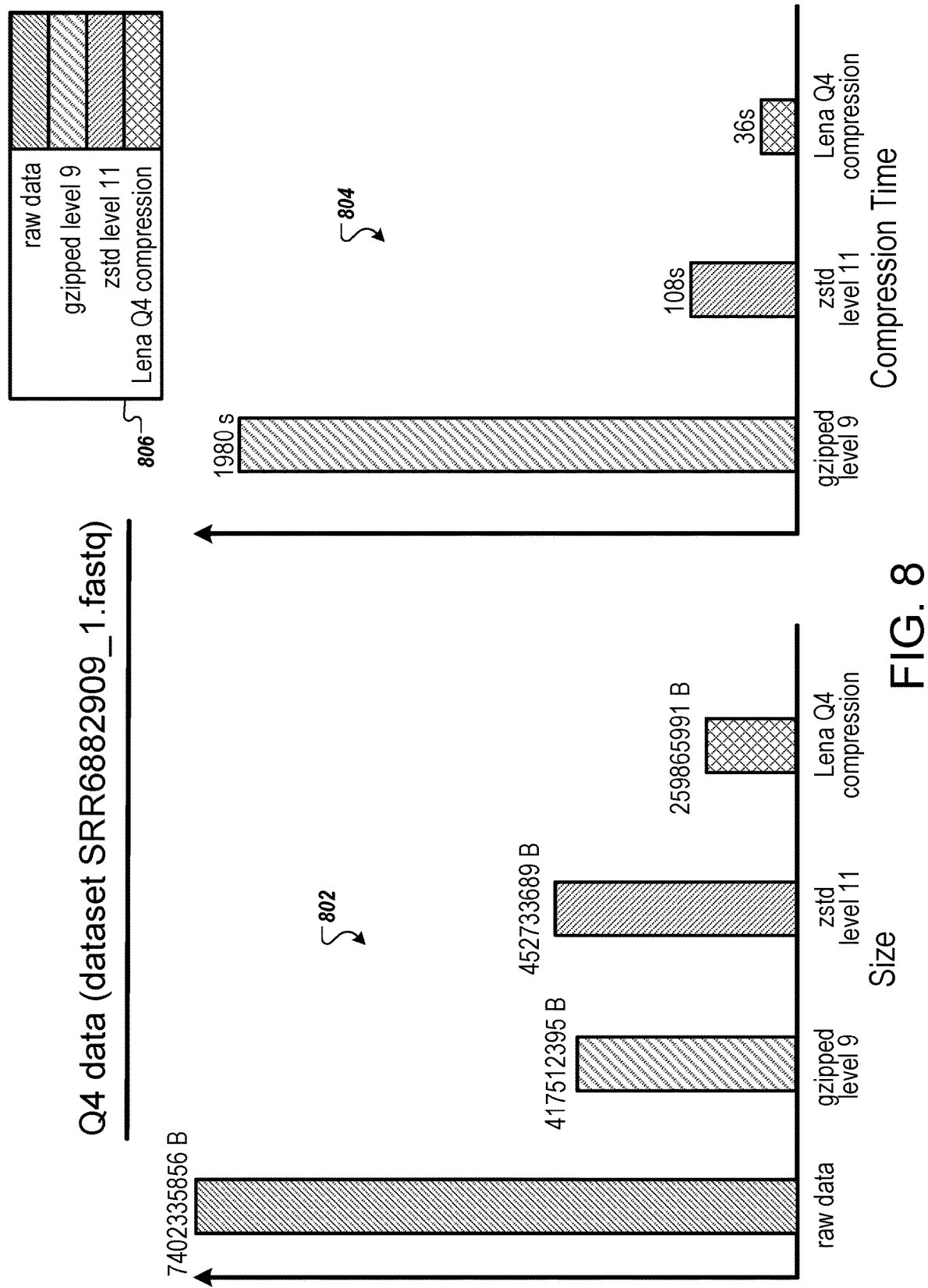
FIG. 8 is a graphical depiction of experimental results of a process for encoding a sequence of quality scores having a first data format

FIG. 8 is a graphical depiction of experimental results of a process for encoding, e.g., compressing, a sequence of quality scores having a first data format. FIG. 8 shows results from the compression of a data set "SRR6882909_1.fastq". The data set "SRR6882909_1.fastq" is formatted using the Q4 format described above. Quality scores of the data set "SRR6882909_1.fastq" include 4 unique quality scores. A chart 802 shows relative sizes of the raw data corresponding to the data set "SRR6882909_1.fastq" as well as compressed versions of the data set "SRR6882909_1.fastq" after compression using various techniques including gzipped level 9 compression, zstd level 11 compression, and Lena Q4 compression. The Lena Q4 compression corresponds to the process 100 shown in FIG. 1 and the methods described herein.

The chart 802 shows that the raw data of the data set "SRR6882909_1.fastq" is 7402335856 bytes, the compressed version of the data set "SRR6882909_1.fastq" using gzipped level 9 compression is 417512395 bytes, the compressed version of the data set "SRR6882909_1.fastq" using zstd level 11 compression is 452733689 bytes, and the compressed version of the data set "SRR6882909_1.fastq" using the Lena Q4 compression is 259865991 bytes. The compression obtained by the Lena Q4 compression of the data set "SRR6882909_1.fastq" is greater than the compression achieved by other alternative compression methods. A legend 806 shows which bar corresponds to which compression method and which bar corresponds to the raw data of the data set "SRR6882909_1.fastq".

The chart 804 shows compression times for each of the compression methods used on the data set "SRR6882909_1.fastq." The chart 804 shows that the compressed version of the data set "SRR6882909_1.fastq" using gzipped level 9 compression takes 1980 seconds to generate, the compressed version of the data set "SRR6882909_1.fastq" using zstd level 11 compression takes 108 seconds to generate, and the compressed version of the data set "SRR6882909_1.fastq" using the Lena Q4 compression takes 36 seconds to generate. The time to compress the data set "SRR6882909_1.fastq" using the Lena Q4 compression is less than the compression time achieved by the other alternative compression methods.

Figure 9:
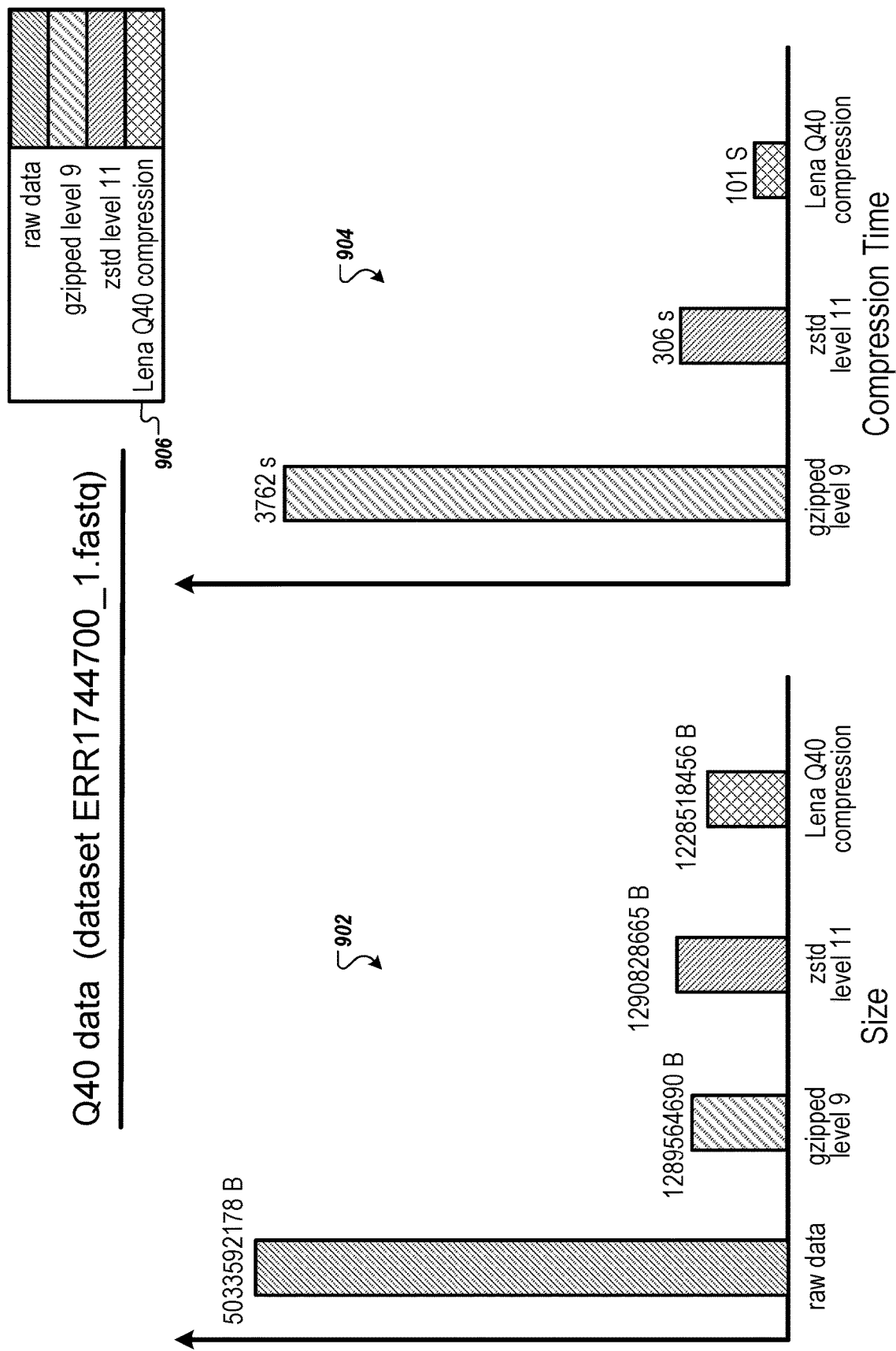
FIG. 9 is a graphical depiction of experimental results of a process for encoding a sequence of quality scores having a second data format

FIG. 9 is a graphical depiction of experimental results of a process for encoding, e.g., compressing, a sequence of quality scores having a second data format. FIG. 9 shows results from the compression of a data set "ERR1744700_1.fastq". The data set "ERR1744700_1.fastq" is formatted using the Q40 format described above. Quality scores of the data set "ERR1744700_1.fastq" include more than 4 unique quality scores. A chart 902 shows relative sizes of the raw data corresponding to the data set "ERR1744700_1.fastq" as well as compressed versions of the data set "ERR1744700_1.fastq" after compression using various techniques including gzipped level 9 compression, zstd level 11 compression, and Lena Q40 compression. The Lena Q40 compression corresponds to the process 300 shown in FIG. 3.

The chart 902 shows that the raw data of the data set "ERR1744700_1.fastq" is 5033592178 bytes, the compressed version of the data set "ERR1744700_1.fastq" using gzipped level 9 compression is 1289564690 bytes, the compressed version of the data set "ERR1744700_1.fastq" using zstd level 11 compression is 1290828665 bytes, and the compressed version of the data set "ERR1744700_1.fastq" using the Lena Q40 compression is 1228518456 bytes. The compression obtained by the Lena Q40 compression of the data set "ERR1744700_1.fastq" is greater than the compression achieved by other alternative compression methods. A legend 906 shows which bar corresponds to which compression method and which bar corresponds to the raw data of the data set "ERR1744700_1.fastq".

The chart 904 shows compression times for each of the compression methods used on the data set "ERR1744700_1.fastq." The chart 904 shows that the compressed version of the data set "ERR1744700_1.fastq" using gzipped level 9 compression takes 3762 seconds to generate, the compressed version of the data set "ERR1744700_1.fastq" using zstd level 11 compression takes 306 seconds to generate, and the compressed version of the data set "ERR1744700_1.fastq" using the Lena Q40 compression takes 101 seconds to generate. The time to compress the data set "ERR1744700_1.fastq" using the Lena Q40 compression is less than the compression time achieved by the other alternative compression methods.

Figure 10:
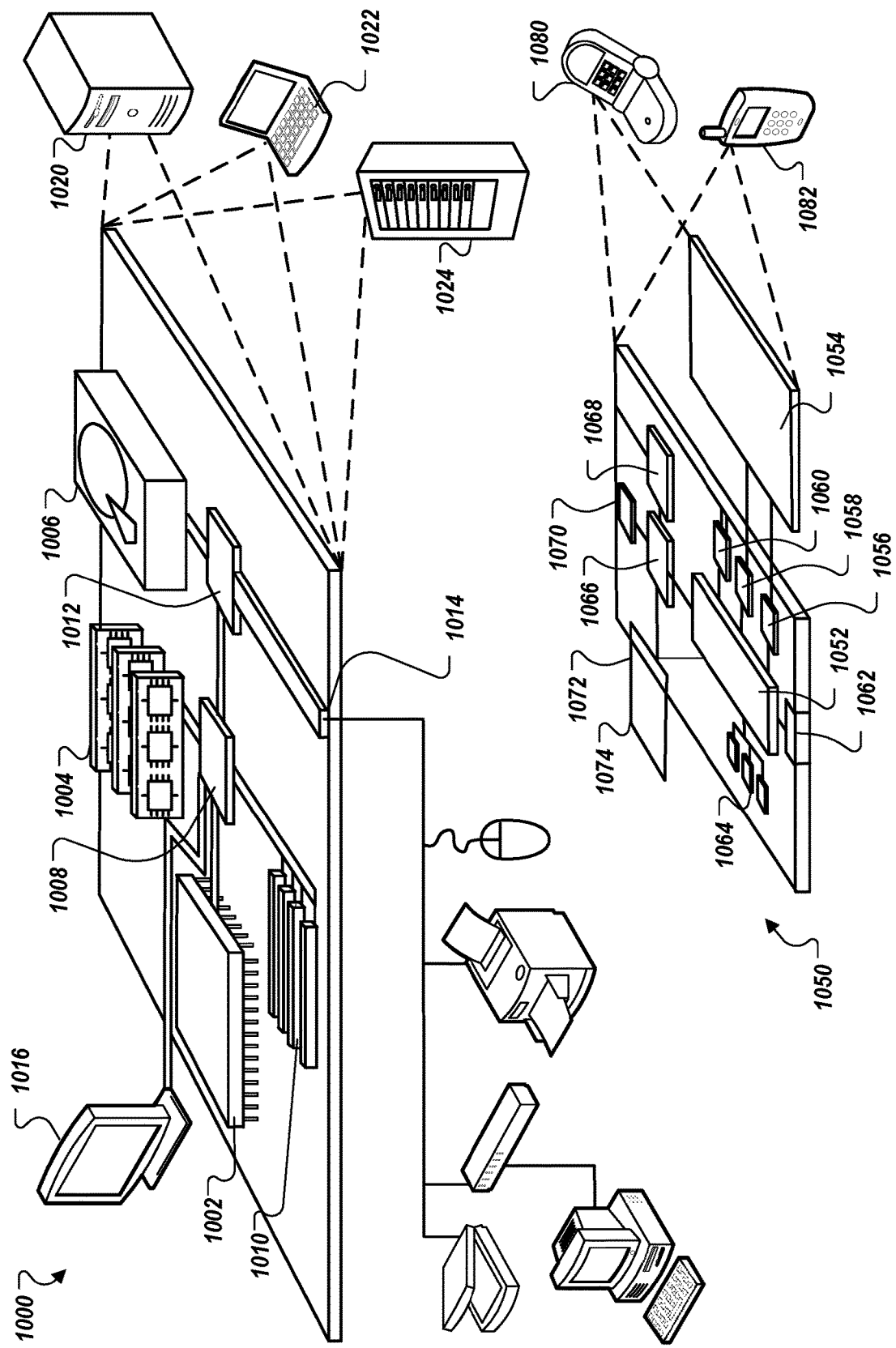
FIG. 10 is a diagram of computer system components that can be used to implement a process for encoding a sequence of quality scores having a first data format.

FIG. 10 is a diagram of computer system 1000 components that can be used to implement a system for generating medical analysis using a joint model based on multivariate ordinal data.

Computing device 1000 is intended to represent various forms of digital computers, such as laptops, desktops, workstations, personal digital assistants, servers, blade servers, mainframes, and other appropriate computers. Computing device 1050 is intended to represent various forms of mobile devices, such as personal digital assistants, cellular telephones, smartphones, and other similar computing devices. Additionally, computing device 1000 or 1050 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 1000 includes a processor 1002, memory 1004, a storage device 1008, a high-speed interface 1008 connecting to memory 1004 and high-speed expansion ports 1010, and a low speed interface 1012 connecting to low speed bus 1014 and storage device 1008. Each of the components 1002, 1004, 1008, 1008, 1010, and 1012, are interconnected using various busses, and can be mounted on a common motherboard or in other manners as appropriate. The processor 1002 can process instructions for execution within the computing device 1000, including instructions stored in the memory 1004 or on the storage device 1008 to display graphical information for a GUI on an external input/output device, such as display 1016 coupled to high speed interface 1008. In other implementations, multiple processors and/or multiple buses can be used, as appropriate, along with multiple memories and types of memory. Also, multiple computing devices 1000 can be connected, with each device providing portions of the necessary operations, e.g., as a server bank, a group of blade servers, or a multi-processor system.

The memory 1004 stores information within the computing device 1000. In one implementation, the memory 1004 is a volatile memory unit or units. In another implementation, the memory 1004 is a non-volatile memory unit or units. The memory 1004 can also be another form of computer-readable medium, such as a magnetic or optical disk.

The storage device 1008 is capable of providing mass storage for the computing device 1000. In one implementation, the storage device 1008 can be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 1004, the storage device 1008, or memory on processor 1002.

The high-speed controller 1008 manages bandwidth-intensive operations for the computing device 1000, while the low speed controller 1012 manages lower bandwidth intensive operations. Such allocation of functions is only an example. In one implementation, the high-speed controller 1008 is coupled to memory 1004, display 1016, e.g., through a graphics processor or accelerator, and to high-speed expansion ports 1010, which can accept various expansion cards (not shown). In the implementation, low-speed controller 1012 is coupled to storage device 1008 and low-speed expansion port 1014. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 1000 can be implemented in a number of different forms, as shown in the figure. For example, it can be implemented as a standard server 1020, or multiple times in a group of such servers. It can also be implemented as part of a rack server system 1024. In addition, it can be implemented in a personal computer such as a laptop computer 1022. Alternatively, components from computing device 1000 can be combined with other components in a mobile device (not shown), such as device 1050. Each of such devices can contain one or more of computing device 1000, 1050, and an entire system can be made up of multiple computing devices 1000, 1050 communicating with each other.

The computing device 1000 can be implemented in a number of different forms, as shown in the figure. For example, it can be implemented as a standard server 1020, or multiple times in a group of such servers. It can also be implemented as part of a rack server system 1024. In addition, it can be implemented in a personal computer such as a laptop computer 1022. Alternatively, components from computing device 1000 can be combined with other components in a mobile device (not shown), such as device 1050. Each of such devices can contain one or more of computing device 1000, 1050, and an entire system can be made up of multiple computing devices 1000, 1050 communicating with each other.

Computing device 1050 includes a processor 1052, memory 1064, and an input/output device such as a display 1054, a communication interface 1066, and a transceiver 1068, among other components. The device 1050 can also be provided with a storage device, such as a micro-drive or other device, to provide additional storage. Each of the components 1050, 1052, 1064, 1054, 1066, and 1068, are interconnected using various buses, and several of the components can be mounted on a common motherboard or in other manners as appropriate.

The processor 1052 can execute instructions within the computing device 1050, including instructions stored in the memory 1064. The processor can be implemented as a chipset of chips that include separate and multiple analog and digital processors. Additionally, the processor can be implemented using any of a number of architectures. For example, the processor 1010 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 1050, such as control of user interfaces, applications run by device 1050, and wireless communication by device 1050.

Processor 1052 can communicate with a user through control interface 1058 and display interface 1056 coupled to a display 1054. The display 1054 can be, for example, a TFT (Thin-Film-Transistor Liquid Crystal Display) display or an OLED (Organic Light Emitting Diode) display, or other appropriate display technology. The display interface 1056 can comprise appropriate circuitry for driving the display 1054 to present graphical and other information to a user. The control interface 1058 can receive commands from a user and convert them for submission to the processor 1052. In addition, an external interface 1062 can be provided in communication with processor 1052, so as to enable near area communication of device 1050 with other devices. External interface 1062 can provide, for example, for wired communication in some implementations, or for wireless communication in other implementations, and multiple interfaces can also be used.

The memory 1064 stores information within the computing device 1050. The memory 1064 can be implemented as one or more of a computer-readable medium or media, a volatile memory unit or units, or a non-volatile memory unit or units. Expansion memory 1074 can also be provided and connected to device 1050 through expansion interface 1072, which can include, for example, a SIMM (Single In Line Memory Module) card interface. Such expansion memory 1074 can provide extra storage space for device 1050, or can also store applications or other information for device 1050. Specifically, expansion memory 1074 can include instructions to carry out or supplement the processes described above, and can also include secure information. Thus, for example, expansion memory 1074 can be provided as a security module for device 1050, and can be programmed with instructions that permit secure use of device 1050. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1064, expansion memory 1074, or memory on processor 1052 that can be received, for example, over transceiver 1068 or external interface 1062.

Device 1050 can communicate wirelessly through communication interface 1066, which can include digital signal processing circuitry where necessary. Communication interface 1066 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 1068. In addition, short-range communication can occur, such as using a Bluetooth, Wi-Fi, or other such transceiver (not shown). In addition, GPS (Global Positioning System) receiver module 1070 can provide additional navigation- and location-related wireless data to device 1050, which can be used as appropriate by applications running on device 1050.

Device 1050 can also communicate audibly using audio codec 1060, which can receive spoken information from a user and convert it to usable digital information. Audio codec 1060 can likewise generate audible sound for a user, such as through a speaker, e.g., in a handset of device 1050. Such sound can include sound from voice telephone calls, can include recorded sound, e.g., voice messages, music files, etc. and can also include sound generated by applications operating on device 1050.

The computing device 1050 can be implemented in a number of different forms, as shown in the figure. For example, it can be implemented as a cellular telephone 1080. It can also be implemented as part of a smartphone 1082, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes, operations, and/or logic flows described in this specification can be performed by one or more central processing units (CPUs) or graphical processing units (GPU) executing one or more computer software instructions to realize the functionality of the processes, operations, and/or logic flows described herein. The processes, operations, and/or logic flows can also be performed in hardware circuitry. For example, in some implementations operations of the present disclosure can be executed by processing engines implemented using logic gates of a field programmable gate array (FPGA) that have been programmatically configured to realize the functionality of the processes, operations, and/or logic flows described herein. By way of another example, operations of the present disclosure can be executed by processing engines implemented using logic gates of an application-specific integrated circuit (ASIC) that have been configured to realize the functionality of the processes, operations, and/or logic flows described herein. In yet other implementations, some of the processes, operations, and/or portions of logic flows may be implemented by one or more CPUs or one or more GPUs and some of the processes, operations, and/or portions of the logic flows may be implemented by hardware circuitry and in any order.

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

OTHER EMBODIMENTS

Particular embodiments of the invention have been described. Other embodiments are within the scope of the following claims. For example, the steps recited in the claims can be performed in a different order and still achieve desirable results.

The invention claimed is:

1. A system for compressing nucleic acid sequence data, the system comprising:
one or more data processing apparatus; and
one or more non-transitory computer-readable storage devices having stored thereon instructions that, when executed by the one or more data processing apparatus, cause the one or more data processing apparatus to perform operations, the operations comprising:
obtaining nucleic acid sequence data representing:
(i) a read sequence comprising data that corresponds to a plurality of base calls generated by a nucleic acid sequencing device, and
(ii) a plurality of quality scores, wherein each quality score of the plurality of quality scores indicates a likelihood that a particular base call of the read sequence was correctly generated by a nucleic acid sequencing device;
determining whether the read sequence includes at least one "N" base;
based on a determination that the read sequence includes at least one "N" base, generating a first encoding data set by using a first encoding process to encode each set of four quality scores of the read sequence into a single byte of memory; and
using a second encoding process to encode the first encoding data set.

2. The system of claim 1, the operations comprising:
based on a determination that the read sequence does not include at least one "N" base, generating a third encoded data set by using a third encoding process to encode each of the quality scores of the read sequence using a base-(x minus 1) number, where x is an integer representing a number of different quality scores used by the nucleic acid sequencing device; and
using a fourth encoding process to encode the third encoding data set.

3. The system of claim 1, wherein x is equal to 3.

4. The system of claim 3, wherein the first encoding process comprises encoding each set of five quality scores of the plurality of quality scores of the read sequence into a single byte by representing each quality score of the set of five quality scores as a base-3 number.

5. The system of claim 1, the operations comprising:
based on a determination that the read sequence includes at least one "N" base, generating a second encoding data set by using a third encoding process to encode each set of four quality scores of the read sequence into a single byte of memory; and
using a fourth encoding process to encode the second encoding data.

6. The system of claim 5, wherein the second encoding process and the fourth encoding process are the same.

7. The system of claim 1, wherein the obtained data includes a FASTQ file.

8. The system of claim 1, wherein the first encoded data set is a compressed version of the plurality of quality scores.

9. The system of claim 1, wherein the second encoding process is a compression process.

10. The system of claim 9, wherein the compression process comprises a Prediction by Partial Matching (PPMD) implementation of a range encoder.

11. The system of claim 10, wherein, for a given value of the first encoded data set, the given value is compressed according to a 4-bit context relative to the position of the given value within the first encoded data set.

12. A method for compressing nucleic acid sequence data, the method comprising:
obtaining, by one or more computers, nucleic acid sequence data representing:
(i) a read sequence comprising data that corresponds to a plurality of base calls generated by a nucleic acid sequencing device, and
(ii) a plurality of quality scores, wherein each quality score of the plurality of quality scores indicates a likelihood that a particular base call of the read sequence was correctly generated by a nucleic acid sequencing device;
determining, by one or more computers, whether the read sequence includes at least one "N" base;
based on a determination that the read sequence includes at least one "N" base, generating, by one or more computers, a first encoding data set by using a first encoding process to encode each set of four quality scores of the read sequence into a single byte of memory; and
using, by one or more computers, a second encoding process to encode the first encoding data set.

13. The method of claim 12, the method further comprising:
based on a determination that the read sequence does not include at least one "N" base, generating a third encoded data set by using a third encoding process to encode each of the quality scores of the read sequence using a base-(x minus 1) number, where x is an integer representing a number of different quality scores used by the nucleic acid sequencing device; and
using a fourth encoding process to encode the third encoding data set.

14. The method of claim 12, wherein x is equal to 3.

15. The method of claim 14, wherein the first encoding process comprises encoding each set of five quality scores of the plurality of quality scores of the read sequence into a single byte by representing each quality score of the set of five quality scores as a base-3 number.

16. The method of claim 12, further comprising:
based on a determination that the read sequence includes at least one "N" base, generating a second encoding data set by using a third encoding process to encode each set of four quality scores of the read sequence into a single byte of memory; and
using a fourth encoding process to encode the second encoding data.

17. A non-transitory computer-readable storage device having stored thereon instructions, which, when executed by a data processing apparatus, cause the data processing apparatus to perform operations, the operations comprising:
obtaining nucleic acid sequence data representing:

(i) a read sequence comprising data that corresponds to a plurality of base calls generated by a nucleic acid sequencing device, and (ii) a plurality of quality scores, wherein each quality score of the plurality of quality scores indicates a likelihood that a particular base call of the read sequence was correctly generated by a nucleic acid sequencing device;

determining whether the read sequence includes at least one "N" base;

based on a determination that the read sequence includes at least one "N" base, generating a first encoding data set by using a first encoding process to encode each set of four quality scores of the read sequence into a single byte of memory; and using a second encoding process to encode the first encoding data set.

18. The computer-readable storage device of claim 17, the operations comprising:

based on a determination that the read sequence does not include at least one "N" base, generating a third encoded data set by using a third encoding process to encode each of the quality scores of the read sequence using a base-(x minus 1) number, where x is an integer representing a number of different quality scores used by the nucleic acid sequencing device; and using a fourth encoding process to encode the third encoding data set.

19. The computer-readable storage device of claim 17, wherein x is equal to 3, and wherein the first encoding process comprises encoding each set of five quality scores of the plurality of quality scores of the read sequence into a single byte by representing each quality score of the set of five quality scores as a base-3 number.

20. The computer-readable storage device of claim 17, the operations comprising:

based on a determination that the read sequence includes at least one "N" base, generating a second encoding data set by using a third encoding process to encode each set of four quality scores of the read sequence into a single byte of memory; and using a fourth encoding process to encode the second encoding data.

* * * * *